(12) United States Patent  (10) Patent No.: US 8,597,904 B2
Bachmann et al.  (45) Date of Patent: Dec. 3, 2013

(54) PHARMACEUTICAL COMPOSITIONS FOR THE TREATMENT OF CONDITIONS RESPONSIVE TO PROTEASOME INHIBITION

(75) Inventors: Andre S. Bachmann, Waipahu, HI (US); Robert Dudler, Uster (CH); Michael Groll, Munich (DE)

(73) Assignee: Pono Corporation, Honolulu, HI (US)

( * ) Notice: Subject to any disclaimer, the term of this patent is extended or adjusted under 35 U.S.C. 154(b) by 232 days.

(21) Appl. No.: 12/742,921

(22) PCT Filed: Nov. 14, 2008

(86) PCT No.: PCT/US2008/083705
§ 371 (c)(1),
(2), (4) Date: Jun. 8, 2010

(87) PCT Pub. No.: WO2009/065090
PCT Pub. Date: May 22, 2009

(65) Prior Publication Data
US 2010/0267070 A1    Oct. 21, 2010

Related U.S. Application Data

(60) Provisional application No. 60/988,409, filed on Nov. 15, 2007, provisional application No. 60/988,054, filed on Nov. 14, 2007.

(51) Int. Cl.
*C12Q 1/37* (2006.01)
*C12N 5/00* (2006.01)
*A61K 31/395* (2006.01)

(52) U.S. Cl.
USPC ............................ 435/23; 435/375; 514/183

(58) Field of Classification Search
None
See application file for complete search history.

(56) References Cited

U.S. PATENT DOCUMENTS 5,096,884 A    3/1992    Numata et al.

FOREIGN PATENT DOCUMENTS

WO    WO 2011/069045    6/2011

OTHER PUBLICATIONS

Proteasome-Glo™ Assay Systems. Proteasome-Glo Assay Systems™. Jun. 2006. Promega Technical Bulletin. pp. 1-17.*
Brünger, et al. 1998. *Acta Crystallogr. D Biol. Crystallogr.* 54: 905-921.
Davidoff, et al. 1992. *Oncogene*. 7:127-133.
Fenteany, et al. 1995. *Science*. 268:726-731.
Geerts, et al. 2007. *Clinical Cancer Research*. 13(21): 6312-6319.
Goldberg & Lau, 1993. *Biochem. J.* 295:735-742.
Groll and Huber. 2005. *Methods Enzymol*. 398:329-336.
Groll, et al. 1997. *Nature*. 386:463-471.
Groll, et al. 2008. *Nature*. 452:755-758.
Gross. 1985. *J. Appl Bacteriol*. 58:167-174.
Heiligtag, et al. 2002. *Cell Death Differ*. 9:1017-1025.
Hirano, et al. 2000. *Microbiol. Mol. Biol. Rev.* 64:624-653.
McKenzie, et al. 1999. *Clin. Cancer Res.* 5:4199-4207.

(Continued)

*Primary Examiner* — Anne Gussow
*Assistant Examiner* — Channing S Mahatan
(74) *Attorney, Agent, or Firm* — Knobbe Martens Olson & Bear, LLP

(57) ABSTRACT

The invention disclosed herein generally relates to methods and compositions for inhibiting proteasome activity comprising a syrbactin compound have the structure of Formula (I) or (II).

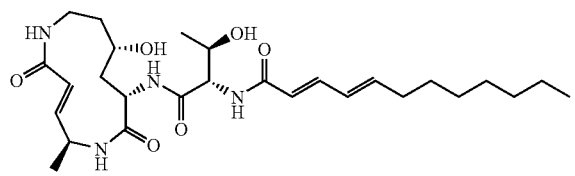

(I)

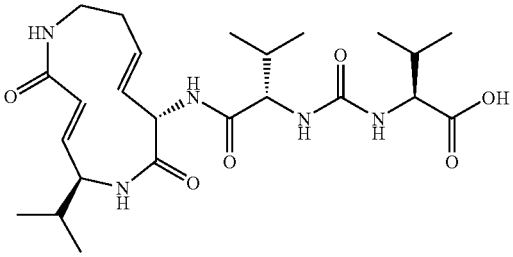

(II)

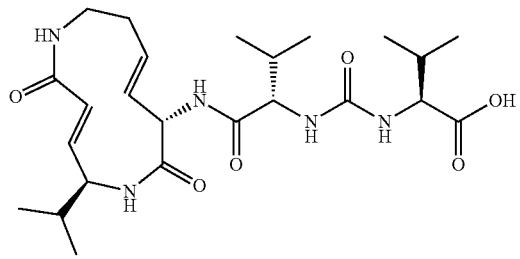

Syringolin A (SylA)

A

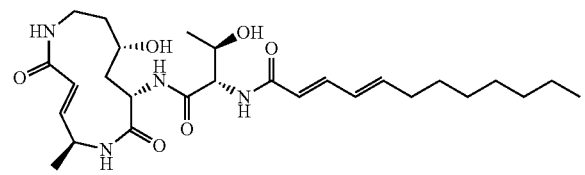

Glidobactin A (GlbA)

B

7 Claims, 20 Drawing Sheets

(56) References Cited

OTHER PUBLICATIONS

Meng, et al. 1999. *Proc. Natl. Acad. Sci. U.S.A.* 96:10403-10408.
Mo and Gross. 1991. *J. Bacteriol.* 173:5784-5792.
Oka, et al. 1988. *J. Antibiot.* 41:1906-1909.
Otwinowski and Minor. 1997. *Methods Enzymol.* 276:307-326.
Potterton, et al. 2003. *Acta Crystallogr. D Biol. Crystallogr.* 59:1131-1137.
Schellenberg, et al. 2007. *Env. Microbiol.* 9:1640-50.
Skehan, et al. 1990. *J. Natl. Cancer Inst.* 82:1107-1112.
Titus and Roundy. 1990. *J. Ind. Microbiol.* 6:215-218.
Turk, D. 1992. "Improvement of a program for molecular graphics and manipulation of electron densities and its application for protein structure determination." *Thesis. Technische Universitaet Muenchen.*
Tweddle, et al. 2001. *Am. J. Pathol.* 158:2067-2077.
Tweddle, et al. 2001. *Cancer Res.* 61:8-13.
Tweddle, et al. 2003. *Cancer Lett.* 197:93-98.
Wallick, et al. 2005. *Oncogene.* 24:5606-5618.
Wang, et al. 2005. *Oncogene.* 24:3574-3582.
Waspi, et al. 1998. *Mol Plant Microbe Interact.* 11:727-733.
Waspi, et al. 1999. *Microbiol Res.* 154:89-93.
Waspi, et al. 2001. *Plant Cell.* 13:153-161.
J. Adams, "Preclinical and clinical evaluation of proteasome inhibitor PS-341 for the treatment of cancer." Curr Opinion in Chem Biol. 2002; 6(4), pp. 493-500.
Hans Amrein, "Functional Analysis of Genes Involved in the Synthesis of Syringolin a by *Pseudomonas* syringae pv. syringae B301 D-R." Molecular Plant-Microbe Interactions. Jan. 2004, 17(1), pp. 90-97.
C.S. Coleman et al., "Syringolin A, a new plant elicitor from the phytopathogenic bacterium *Pseudomonas* syringae pv. syringae, inhibits the proliferation of neuroblastoma and ovarian cancer cells and induces apoptosis." Cell proliferation. 39(6), pp. 599-609, published online Nov. 15, 2006.
L. Hasfored et al., "Mechanism of embryonal tumor initiation: Distinct roles for MycN expression and MYCN amplification." PNAS. Aug. 24, 2004; 101(34), pp. 12664-12669.

Michaelis et al., "Anti-cancer effects of bortezomib against chemoresistant neuroblastoma cell lines in vitro and in vivo." International J Oncology. 2006; 28, pp. 439-446.
M. Norris et al., "Expression on N-myc and MRP Genes and Their Relationship to N-myc gene Dosage and Tumor Formation in a Murine Neuroblastoma Model." Medical Pediatric Oncology. 2000; 35, pp. 585-589.
Kei-ichi Numata et al., "Enzymatic Formation of Glidobactamine: A Peptide Nucleus of Glidobactins A, B and C, New Lipopeptide Antitumor Antibiotics," The Journal of Antibiotics, 1988, vol. XLI, No. 10, pp. 1351-1357.
Masahisa Oka et al., "Glidobactins A, B and C, New Antitumor Antibiotics. I. Production, Isolation, Chemical Properties and Biological Activity." The Journal of Antibiotics (Tokyo), Oct. 1988, 41(10), pp. 1331-1337.
Masahisa Oka et al., "Glidobactins A, B and C, New Antitumor Antibiotics. II. Structure Elucidation," The Journal of Antibiotics (Tokyo), Oct. 1988, 41(10), pp. 1338-1350.
W. Weiss et al., "Genomic-wide Screen for Allelic Imbalance in a Mouse Model for Neuroblastoma." Cancer Res. May 1, 2000; 60, pp. 2483-2487.
W. Weiss et al., "Targeted expression of MYCN causes neuroblastoma in transgenic mice." EMBO J. 1997; 16(11), pp. 2985-2995.
ISA/KR, "International Search Report and Written Opinion of the International Searching Authority," corresponding International Application No. PCT/US2008/083705, mailed on May 22, 2009, 8 pages.
Borissenko et al., 20S Proteasome and Its Inhibitors: Crystallographic Knowledge for Drug Development, Chem. Rev., vol. 107: 687-717 (2007).
Chesler et al., Malignant Progression and Blockade of Angiogenesis in a Murine Transgenic Model of Neuroblastoma, Cancer Res., vol. 67(19): 9435-9442 (2007).
Clerc, et al., Synthetic and Structural Studies on Syringolin A and B Reveal Critical Determinants of Selectivity and Potency of Proteasome Inhibition, PNAS, vol. 106(16):6507-6512 (2009).

\* cited by examiner

A     Syringolin A (SylA)

B     Glidobactin A (GlbA)

Fig. 1

PHARMACEUTICAL COMPOSITIONS FOR THE TREATMENT OF CONDITIONS RESPONSIVE TO PROTEASOME INHIBITION

FIELD OF THE INVENTION

The invention disclosed herein generally relates to syringolins and glidobactins and their use as proteasome inhibitors in methods of treating various diseases and pathological conditions. Embodiments of the invention further relate to pharmaceutical formulations comprising syringolins and glidobactins for use in the treatment of various diseases and pathological conditions that respond to the action of proteasome inhibitors.

BACKGROUND

Pathological conditions resulting from the hyperproliferation of cells, such as cancer, are a leading cause of death in humans. Current treatment protocols for pathological conditions caused by inappropriate cell proliferation include chemotherapy and radiation. Although these treatment protocols have met with some success, there is a continuing need for drugs that can effectively treat diseases caused by uncontrollable cell growth. Proteasome inhibitors are a new class of promising inhibitors which appear to be more effective and active in cancer cells compared with normal cells, thus providing a distinct advantage over other drugs which do not distinguish between cancerous and normal cells. Proteasome inhibitors are also considered useful for the treatment of many other diseases and pathological conditions.

SUMMARY OF THE INVENTION

Embodiments of the present invention relate to methods and compositions for inhibiting proteasome activity comprising a syrbactin compound having the structure of Formula I or II:

Formula I

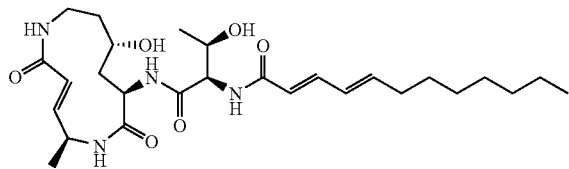

Formula II

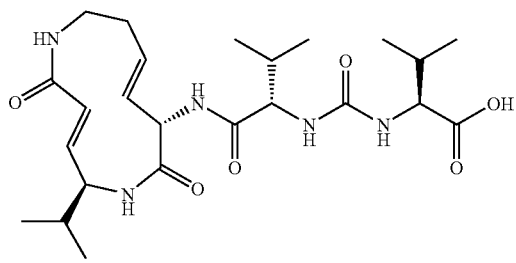

In embodiments of the invention, a method for inhibiting proteasome activity in a cell is provided, comprising: contacting a cell with an amount of a compound of Formula I, or an analogue or derivative thereof, wherein the amount of compound is effective to inhibit proteasome activity of said cell. In some embodiments, inhibition of proteasome activity is confirmed using an in vitro proteasome inhibition assay.

In some embodiments, the compound of Formula I, or analogue or derivative thereof, inhibits a chymotrypsin-like activity of a proteasome of the cell. In some embodiments, inhibition of the chymotrypsin-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula I, or analogue or derivative thereof, inhibits a trypsin-like activity of a proteasome of the cell. In some embodiments, inhibition of the trypsin-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula I, or analogue or derivative thereof, inhibits a caspase-like activity of a proteasome of the cell. In some embodiments, inhibition of the caspase-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula I, or analogue or derivative thereof, inhibits at least one protease-like activity of a proteasome of the cell, wherein the protease-like activity is selected from the group of: chymotrypsin-like activity, trypsin-like activity and caspase-like activity. In some embodiments, inhibition of the at least one protease-like activity comprises interaction of the double bond at the 3,4 position of the compound with the threonine residue of the catalytic site of the proteasome of the cell. In some embodiments, the interaction, of the double bond at the 3,4 position of the compound with the threonine residue of the catalytic site is a binding interaction.

In some embodiments, the compound of Formula I is glidobactin A, or an analogue or derivative thereof.

In embodiments of the invention, a method for inhibiting proteasome activity in a cell is provided, comprising: contacting a cell with an amount of a compound of Formula II, or analogues or derivatives thereof, wherein the amount of compound is effective to inhibit proteasome activity of said cell. In some embodiments, inhibition of proteasome activity is confirmed using an in vitro proteasome inhibition assay.

In some embodiments, the compound of Formula II, or analogue or derivative thereof, inhibits a chymotrypsin-like activity of a proteasome of the cell. In some embodiments, inhibition of the chymotrypsin-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula II, or analogue or derivative thereof, inhibits a trypsin-like activity of a proteasome of the cell. In some embodiments, inhibition of the trypsin-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula II, or analogue or derivative thereof, inhibits a caspase-like activity of a proteasome of the cell. In some embodiments, inhibition of the caspase-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula II, or analogue or derivative thereof, inhibits at least one protease-like activity of a proteasome of the cell, wherein the protease-like activity is selected from the group of: chymotrypsin-like activity, trypsin-like activity and caspase-like activity. In some embodiments, inhibition of the at least one protease-like activity comprises interaction of the double bond at the 3,4 position of the compound with the threonine residue of the catalytic site of the proteasome of the cell. In some embodiments, the interaction of the double bond at the 3,4 position of the compound with the threonine residue of the catalytic site is a binding interaction.

In some embodiments, the compound of Formula II is syringolin A, or an analogue or derivative thereof.

Embodiments of the present invention also relate to methods and compositions for inducing apoptosis of tumor cells comprising a syrbactin compound having the structure of Formula I or II, or analogues or derivatives thereof.

In embodiments of the invention, a method for inducing apoptosis of tumor cells is provided, comprising: contacting said tumor cells with an amount of a compound of Formula I, or an analogue or derivative thereof, wherein the amount of compound is effective to inhibit induce apoptosis. In some embodiments, induction of apoptosis is assayed by at least one assay selected from the following group: in vitro proliferation assays, p53 protein level assays, PARP cleavage assays, phosphatidyl serine extraversion assays and autophagy induction assays.

In embodiments of the invention, a method for inducing apoptosis of a tumor cell is provided, comprising: administering to tumor cells a compound of Formula I, or an analogue or derivative thereof, wherein the compound covalently attaches to the threonine residue of a chymotrypsin-like catalytic site of a proteasome of the cells. In some embodiments, the covalent attachment inhibits a chymotrypsin-like activity of the proteasome.

In embodiments of the invention, a method for inducing apoptosis of a tumor cell is provided, comprising: administering to tumor cells a compound of Formula I, or an analogue or derivative thereof, wherein the compound covalently attaches to the threonine residue of a trypsin-like catalytic site of a proteasome of the cells. In some embodiments, the covalent attachment inhibits a trypsin-like activity of the proteasome.

In embodiments of the invention, a method for inducing apoptosis of a tumor cell is provided, comprising: administering to tumor cells a compound of Formula I, or an analogue or derivative thereof, wherein the compound covalently attaches to the threonine residue of a caspase-like catalytic site of a proteasome of the cells. In some embodiments, the covalent attachment inhibits a caspase-like activity of the proteasome.

In embodiments of the invention, a method for inducing apoptosis of tumor cells is provided, comprising: administering to tumor cells a compound of Formula I, or an analogue or derivative thereof, wherein the compound covalently attaches to the threonine residue of at least one catalytic site of a proteasome of the cells selected from the group of: a chymotrypsin-like catalytic site, a trypsin-like catalytic site, and a caspase-like catalytic site. In some embodiments, the covalent attachment inhibits the activity of the at least one catalytic site of the proteasome.

In embodiments of the invention, a method for inducing apoptosis of tumor cells is provided, comprising: contacting said tumor cells with an amount of a compound of Formula II, or an analogue or derivative thereof, wherein the amount of compound is effective to inhibit induce apoptosis. In some embodiments, induction of apoptosis is assayed by at least one assay selected from the following group: in vitro proliferation assays, p53 protein level assays, PARP cleavage assays, phosphatidyl serine extraversion assays and autophagy induction assays.

In embodiments of the invention, a method for inducing apoptosis of a tumor cell is provided, comprising: administering to tumor cells a compound of Formula II, or an analogue or derivative thereof, wherein the compound covalently attaches to the threonine residue of a chymotrypsin-like catalytic site of a proteasome of the cells. In some embodiments, the covalent attachment inhibits a chymotrypsin-like activity of the proteasome.

In embodiments of the invention, a method for inducing apoptosis of a tumor cell is provided, comprising: administering to tumor cells a compound of Formula II, or an analogue or derivative thereof, wherein the compound covalently attaches to the threonine residue of a trypsin-like catalytic site of a proteasome of the cells. In some embodiments, the covalent attachment inhibits a trypsin-like activity of the proteasome.

In embodiments of the invention, a method for inducing apoptosis of a tumor cell is provided, comprising: administering to tumor cells a compound of Formula II, or an analogue or derivative thereof, wherein the compound covalently attaches to the threonine residue of a caspase-like catalytic site of a proteasome of the cells. In some embodiments, the covalent attachment inhibits a caspase-like activity of the proteasome.

In embodiments of the invention, a method for inducing apoptosis of tumor cells is provided, comprising: administering to tumor cells a compound of Formula II, or an analogue or derivative thereof, wherein the compound covalently attaches to the threonine residue of at least one catalytic site of a proteasome of the cells selected from the group of: a chymotrypsin-like catalytic site, a trypsin-like catalytic site, and a caspase-like catalytic site. In some embodiments, the covalent attachment inhibits the activity of the at least one catalytic site of the proteasome.

Embodiments of the present invention also relate to methods for screening analogues or derivatives of Formula I or II for inhibition of proteasomal activity.

In embodiments of the invention, a method for screening analogues or derivatives Formula I is provided comprising: confirming the presence of a 12-member ring having a 3,4 double bond; and assaying the compound for inhibition of proteasomal activity. In some embodiments, the inhibition of proteasomal activity by said analogue or derivative comprises interaction between a catalytic subunit of a proteasome and the 3,4 double bond of the 12-member ring of the analogue or derivative.

In embodiments of the invention, a method for screening analogues or derivatives Formula II is provided comprising: confirming the presence of a 12-member ring having a 3,4 double bond; and assaying the compound for inhibition of proteasomal activity. In some embodiments, the inhibition of proteasomal activity by said analogue or derivative comprises interaction between a catalytic subunit of a proteasome and the 3,4 double bond of the 12-member ring of the analogue or derivative.

Embodiments of the invention also relate to compositions comprising a purified compound having the structure of Formula II, or an analogue or derivative thereof. The compositions can be useful for inhibiting proteasomal activity, inducing apoptosis in tumor cells and treating various diseases for which inhibition of proteasomal activity is beneficial. Such diseases include: uncontrolled cell proliferation diseases, cancers and inflammatory diseases.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 is an illustration that depicts the chemical structure of syringolin A (A) and glidobactin A (B)

DETAILED DESCRIPTION OF THE INVENTION

Definitions

Figure 2:
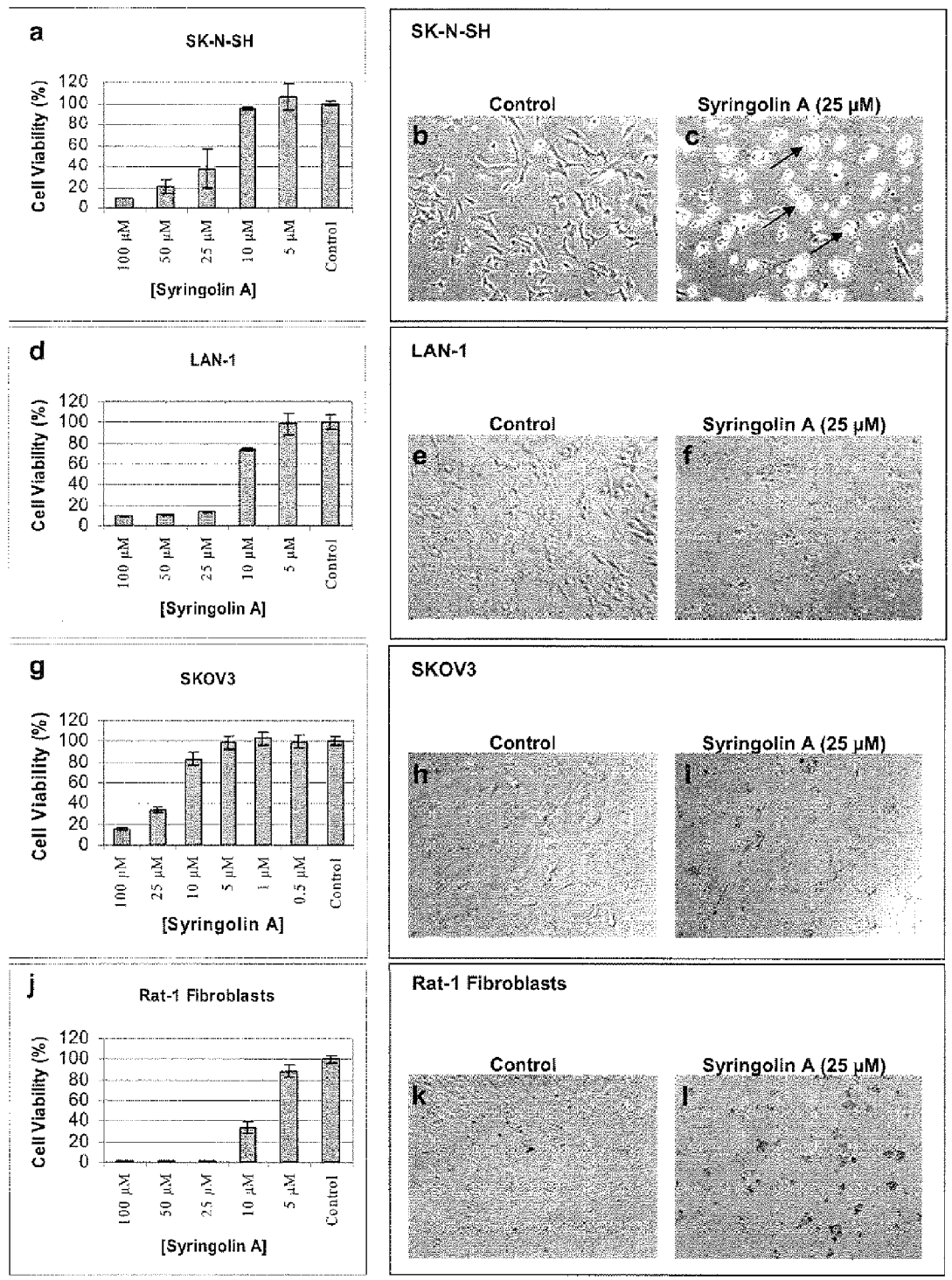
FIG. 2 includes bar graphs and microscope images that depict the effect of syringolin A on the proliferation rate and morphology of mammalian cancer cells.

Unless otherwise noted, terms are to be understood according to conventional usage by those of ordinary skill in the relevant art.

Figure 1:
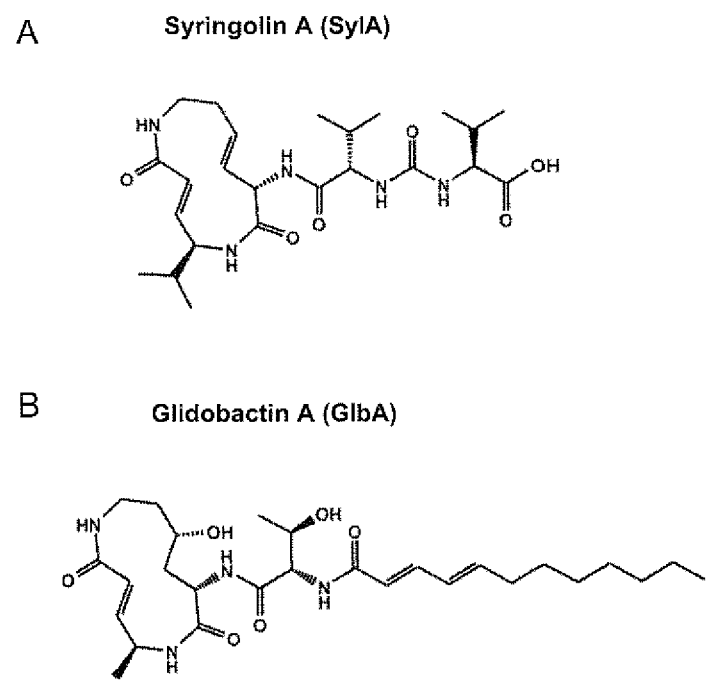

As used herein, the term "syringolin" refers to *Pseudomonas syringae* pv. *syringae* (Pss), a pathogen of many plant species, causing for example brown spot disease on bean (*Phaseolus vulgaris*). In some embodiments, the term includes syringolin derivatives, for example, but not limited to, syringolin A-F. In some embodiments, certain syringolin derivatives, for example, syringolin A, B, C, D, E, or F, are specifically excluded. In some embodiments, the term includes syringolin analogues, either currently known or yet to be discovered, that share a common structure, which includes the 12-membered ring structure containing the double bond at the 3,4 position (FIG. 1A).

As used herein, the term "glidobactin" or "cepafungin" refers to a family of compounds originally identified in culture supernatants of a bacterial strain K481-B101 (ATCC 53080; DSM 7029). In some embodiments, the term includes glidobactin derivatives, for example, but not limited to, glidobactin A-H. In some embodiments, certain glidobactin derivatives, for example, glidobactin A, B, C, D, E, F, G, or H, are specifically excluded. In some embodiments, the term includes glidobactin analogues, either currently known or yet to be discovered, that share a common structure, which includes the 12-membered ring structure containing the double bond at the 3,4 position (FIG. 1B).

As used herein, the term "syrbactin" refers to a novel class of compounds that share a similar chemical core structure (FIG. 1) and irreversibly inhibiting the catalytic activity of eukaryotic prokaryotic proteasomes. Syrbactins can include, but are not limited to, syringolins, for example, but not limited to, syringolin A, and glidobactins, including, but not limited to glidobactin A.

As used herein, a subject includes any organism, including an animal, for whom diagnosis, screening, monitoring or treatment is contemplated. Animals include mammals such as primates and domesticated animals. An exemplary primate is human. A patient refers to a subject such as a mammal, primate, human or livestock subject afflicted with a disease condition or for which a disease condition is to be determined or risk of a disease condition is to be determined.

As used herein, the term "cancer" and "cancerous" when used herein refer to or describe the physiological condition in mammals that is typically characterized by unregulated cell growth. Examples of cancer include, but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, head and neck cancer, ovarian cancer and neuroblastoma. While the term "cancer" as used herein is not limited to any one specific form of the disease, it is believed that the methods of the invention can be effective for cancers which are found to be blood-related cancers and those cancers in which solid tumors form, including, but not limited to, multiple myeloma, mantle cell lymphoma and leukemias.

As used herein, inflammation refers to a condition normally arising due to an immune response to a stimulus, such as, an external or internal insult, for example, an infection (e.g., fungal, parasitic, bacterial or viral), foreign substance or irritation. Inflammation can be local or systemic within an organism and is often characterized by swelling, pain, redness as well as organ dysfunction. Inflammation involves the movement of fluid and cells (e.g., white blood cells or leukocytes, neutrophils, monocytes and T- and B-cells) into the affected area, site or tissue. In some instances, the immune system can trigger an inflammatory response in the absence of a typical insult. Such excessive, misdirected and/or inappropriate immune inflammatory responses can lead to damage of normal, healthy body tissues and are associated with certain diseases and disorders, including, for example, autoimmune diseases and disorders. There are a number of diseases and disorders that can involve inflammation, both neoplastic and non-neoplastic or non-malignant (benign) diseases. Examples of such diseases and disorders include, but are not limited to, arteritis, arthritis, psoriasis, fibroproliferative disorders, restinosis, stenosis, neurodegenerative diseases, sepsis, appendicitis, myocarditis, nephritis, colitis, gastritis, atherosclerosis or arteriosclerosis, inflammatory bowel disease, systemic lupus erythematosis, multiple sclerosis, type 1 diabetes, Crohn's disease, and coronary artery disease.

As used herein, the terms "treating," "treatment," and "therapy" as used herein refer to curative therapy, prophylactic therapy, and preventative therapy. The term "treatment" includes therapeutic treatment as well as prophylactic treatment (either preventing the onset of disorders altogether or delaying the onset of a pre-clinically evident stage of disorders in individual subjects).

As used herein, the phrase "therapeutically-effective" is intended to qualify the amount of each agent that will achieve the goal of improvement in disorder severity and/or the frequency of incidence over treatment, while avoiding adverse side effects typically associated with alternative therapies. For example, effective neoplastic therapeutic agents prolong the survivability of the patient, inhibit the rapidly-proliferating cell growth associated with the neoplasm, or effect a regression of the neoplasm.

As used herein, a "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit proteasome activity.

As used herein, a "synergistic combination" refers to a combination of a first compound and at least a second compound that is considered therapeutically synergistic when the combination treatment regimen produces a significantly better result (e.g., cell growth arrest, tumor size reduction, chemoprevention, apoptosis, cell death) than the additive effects of each constituent when administered alone at a therapeutic dose. Standard statistical analysis can be employed to determine when the results are significantly better. For example, a Mann-Whitney Test or some other generally accepted statistical analysis can be employed.

As used herein, "purified" refers to a composition of syrbactin compound that is at least about 75% pure. In some embodiments, "purified" can refer to a composition of syrbactin compound that is at least about 80% pure. In some embodiments, the term can refer to a composition of syrbactin compound that is at least about 85%, 86%, 87%, 88%, 89%, 90%, 91%, 92%, 93%, 94%, 95%, 96%, 97%, 98% or 99%.

Syrbactin Compounds

Embodiments of the invention relate to the discovery of a novel class of compounds referred to herein as syrbactins, which inhibits proteasome activity by a novel mechanism. Included among the class of syrbactins are a family of closely related peptide derivatives dubbed syringolins, of which syringolin A is a major variant. Syringolins are secreted by the phytopathogenic bacterium *Pseudomonas syringae* pv. *syringae* and are virulence factors that can trigger hypersensitive cell death in mammalian cancer cells and in plant cells colonized by the bacteria. Syrbactins also include the family of compounds called glidobactins, which share a similar chemical core structure with the syringolin family of compounds.

Embodiments of the invention relate to the discovery that syrbactin compounds can irreversibly inhibit the catalytic activity of eukaryotic proteasomes in vivo and in vitro by forming a covalent linkage to the active site of proteasome subunits. Proteasome inhibitors are useful in the treatment of a variety of pathological conditions, including cancer, inflammatory diseases, microbial, viral, and parasitic infections, autoimmune disorders, ischemic stroke, and conditions caused by immunosuppression. Embodiments of the invention provide pharmaceutical compositions and methods for the treatment of such conditions.

Syringolins

*Pseudomonas syringae* pv. *syringae* (Pss) is a pathogen of many plant species, causing for example brown spot disease on bean (*Phaseolus vulgaris*) (Hirano et al. [2000] *Microbial. Mol. Biol. Rev.* 64: 624-653). Some Pss strains secrete syringolin A (SylA), a peptide derivative synthesized by a mixed non-ribosomal peptide synthetase (NRPS)/polyketide synthetase (PKS) encoded by a gene cluster which was previously cloned from the strain Pss B301D-R (Amrein et al. 2004. *Mol. Plant. Microbe Interact.* 17: 90-97, which is incorporated herein by reference in its entirety). Although the syringolin family of peptide derivatives appear to constitute virulence factors, syringolins are determinants recognized and reacted to by nonhost plant species. In addition, syringolin A has been shown to induce hypersensitive death of cells colonized by powdery mildew in wheat and, thus, to reprogram a compatible interaction into an incompatible one (Amrein et al. 2004. *Mol Plant Microbe Interact.* 17:90-97; Waspi et al. 1998. *Mol Plant Microbe Interact.* 11:727-733; Waspi et al. 1999. *Microbial Res.* 154:89-93; Waspi et al. 2001. *Plant Cell* 13:153-161, each of which is incorporated herein by reference in its entirety). Syringolin A is an unusual derivative of a tripeptide that contains a 12-membered ring consisting of the amino acids 5-methyl-4-amino-2-hexenoic acid and 3,4-dehydrolysine, two nonproteinogenic amino acids (FIG. 1A).

Glidobactins

Glidobactins (synonym cepafungins) are a family of compounds structurally related to syringolins that exhibit a broad spectrum of antifungal activity, are cytotoxic to tumor cell lines, and prolong the life span of mice inoculated with P388 leukemia cells (Oka et al. 1988. *J. Antibiot.* 41:1331-1337; Oka et al. 1988. *J. Antibiot.* 41:1906-1909; Oka et al. 1988. *J. Antibiot.* 41:1338-1350, each of which is incorporated herein by reference in its entirety). Glidobactins were identified in culture supernatants of a bacterial strain K481-B101 (ATCC 53080; DSM 7029), which was isolated from Greek soil and designated as the novel species "*Polyangium brachysporum*" (Oka et al. 1988. *J. Antibiot.* 41:1331-1337, which is incorporated herein by reference in its entirety). Glidobactins are acylated tripeptide derivatives that contain a twelve-membered ring structure consisting of the two unique non-proteinogenic amino acids erythro-4-hydroxy-L-lysine and 4(S)-amino-2(E)-pentenoic acid. Sequencing of the 16S rRNA of strain K481-B101 revealed that it belongs to the order Burkholderiales (Schellenberg et al. 2007. *Env. Microbiol.* 9:1640-50, which is incorporated herein by reference in its entirety).

Biosynthetic Pathways to Produce Syrbactins

Embodiments of the invention provide compositions comprising isolated syrbactin compounds and methods for making such.

The genes involved in the biosynthesis of syringolin A and glidobactin A have been identified (Amrein et al. 2004. *Mol. Plant. Microbe Interact.* 17:90-97; Schellenberg et al. 2007. *Env. Microbial.* 9:1640-50, each of which is incorporated herein by reference in its entirety). The identified genes involve proteins consisting of modules typical for nonribosomal peptide synthetases and type I polyketide synthetases as well as proteins likely involved in the transcriptional regulation of syringolin A biosynthesis and in syringolin A export. Furthermore, the structure and arrangement of the modules led to the formulation of a model explaining the synthesis of the tripeptide, including the formation of the two nonproteinogenic amino acids in the ring structure of syringolin. A and glidobactin A, respectively.

*P. syringae* pv. *syringae* strain can be cultured under conditions as described (Gross. 1985. *J Appl Bacteriol* 58:167-174; Mo and Gross. 1991. *J. Bacterial* 173:5784-5792, each of which is incorporated herein by reference in its entirety). Isolation of syringolin is performed as described (Wäspi, et al. 1999. *Microbial Res.* 154:89-93, which is incorporated herein by reference in its entirety).

*Polyangium brachysporum* is cultured under conditions, and glidobactin is isolated, as described (Oka, et al. 1988. *The Journal of Antibiotics* 41(10):1331-1337, which is incorporated herein by reference in its entirety).

Proteasome Inhibition

Embodiments of the invention provide methods for inhibiting the activity of the proteasome using the compounds disclosed herein, including, but not limited to, syringolin A and glidobactin A. These molecules belong to a new class of proteasome inhibitors. Disclosed herein is a novel mechanism of covalent binding to proteasome catalytic subunits by which the compounds disclosed herein, including syringolin A (SylA) and glidobactin A (GlbA), irreversibly inhibit proteasome activity.

Proteasome inhibitors represent a new and promising class of inhibitors with applications in the treatment of cancer and many other pathological and autoinflammatory diseases. Embodiments of the invention thus include compounds, including syringolins, glidobactins, and derivatives thereof as proteasome inhibitors. Further embodiments include pharmaceutical formulations comprising the compounds disclosed herein, including syringolins, glidobactins, and derivatives and analogs thereof for use in the treatment of various pathological conditions.

The compounds disclosed herein can inhibit proteasome activity by irreversibly inhibiting all three types of proteasomal proteolytic sites. The modes of irreversible inhibition include binding of the hydroxy group of the proteasome's threonine residue of a chymotrypsin-like catalytic site by a Michael-type 1,4-addition between Thr1Oγ of the proteasome and the C4 double bond in the 12-membered ring system of the compound. The compounds disclosed herein can also provide further modes of proteasomal inhibition, such as, for example, inhibiting the trypsin- and/or caspase-like activities of the proteasome.

In some embodiments, administration of a compound disclosed herein inhibits proteasome activity by irreversibly inhibiting chymotrypsin-like activity in the eukaryotic 20S proteasome. As disclosed herein (Examples 7 and 9), treatment with a compound disclosed herein, including syringolin and/or glidobactin and derivatives or analogs thereof, leads to specific inhibition of chymotrypsin-like activity in the 20S proteasome.

In some embodiments, administration of the compounds disclosed herein inhibits proteasome activity by irreversibly inhibiting trypsin-like activity in the eukaryotic 20S proteasome. As disclosed herein (Examples 7 and 9), treatment with a syrbactin compound leads to specific inhibition of trypsin-like activity in the 20S proteasome.

In some embodiments, administration of the compounds disclosed herein inhibits proteasome activity by irreversibly inhibiting caspase-like activity in the eukaryotic 20S proteasome. As disclosed herein (Examples 7 and 9), treatment with a syrbactin compound leads to specific inhibition of caspase-like activity in the 20S proteasome.

In some embodiments, administration of the compounds disclosed herein induces inhibition of proteasome activity and leads to the accumulation of ubiquitinated proteins in a cell. As disclosed herein (Examples 8 and 11), treatment with a syrbactin compound leads to an increase in levels of ubiquitinated proteins within cells, indicating inhibition of proteasome activity.

Induction of Apoptosis

Apoptosis is a key mechanism of cell lifespan control important for development, tissue homeostasis, immune system maturation, and cell termination in cases of disease, cell injury, or viral infection. The proteasomal-ubiquitin pathway can have a large role in cell death and survival. Proteasomal inhibitors can trigger apoptosis in proliferating cells as a result of their ability to stabilize positive and negative regulators of cell growth, thereby stimulating conflicting signaling pathways. In many cancer cells, apoptosis is inhibited, thus leading to uncontrolled cell proliferation.

In some embodiments, the compounds disclosed herein provide a selective and cell specific activation of apoptosis by inhibition of proteasomal activity, inducing apoptosis in tumor cells while leaving untransformed cells unharmed. The activity of syringolin A in mammalian cells was recently explored by Coleman et al. (Coleman et al. 2006. *Cell Prolif.* 39:599-609, which is incorporated herein by reference in its entirety). Syringolin A-treated neuroblastoma (NB) cells were demonstrated to strongly react with Annexin V, a reagent that is commonly used to detect apoptotic cells (by binding to phosphatidyl serine, which is present only on the cell surface of apoptotic cells, but not normal cells). In addition, syringolin. A was shown to inhibit the proliferation of NB and ovarian cancer cells in a dose-dependent manner. An IC-50 (concentration at which the cell proliferation rate is reduced to 50%) of approximately 25 µM syringolin A was determined for this inhibitory effect. It was discovered that treatment of NB cells with 25 µM syringolin for 48 hours caused severe morphological changes such as rounding of cells and loss of adherence, both of which are typical changes observed during programmed cell death (apoptosis). Thus, syringolin A was shown to inhibit cell proliferation by induction of apoptosis.

As disclosed herein, the compounds disclosed herein, including SylA, GlbA and derivatives thereof, induce anti-proliferative effects, morphological changes, autophagy and apoptosis in mammalian cancer cell lines. Furthermore, such compounds can reduce tumor size and provide chemoprevention benefits in animal cancer models.

In some embodiments, administration of a compound disclosed herein can inhibit cell proliferation by inducing apoptosis, which can be measured by total protein levels of the tumor suppressor protein p53. The p53 protein is an important regulator and mediator of apoptosis, and increased levels of p53 correspond to a high likelihood of apoptosis. As disclosed herein (Examples 4, 8 and 14), treatment with a syrbactin compound can lead to a rapid increase of p53 levels within cells as early as within about 24 hours of treatment, indicating that the compound is able to activate p53 protein and induce apoptosis.

In some embodiments, administration of a syringolin and/or glidobactin compound can lead to cleavage of poly (ADP-ribose) polymerase (PARP), which occurs during apoptosis. As disclosed herein (Examples 5 and 14), treatment with a syrbactin compound can induce cleavage of PARP in cells within about 24 to about 48 hours, indicating the onset of apoptosis.

In some embodiments, administration of a syrbactin compound leads to induction of extraversion of phosphatidyl serine, an intracellular membrane component which is extraverted in apoptotic cells and displayed on the cell surface. As disclosed herein (Example 6), treatment with a syrbactin compound can induce extraversion of phosphatidyl serine in cells within about 48 hours, indicating the onset of apoptosis.

In some embodiments, administration of a syrbactin compound leads to induction of autophagy within a cell. Syrbactin-induced autophagy can be measured by, for example, levels of microtubule-associated protein 1 light chain 3 (LC3), and in particular, levels of LC3-II, which is a reliable marker of autophagosomes. As disclosed herein (Example 13), treatment with a syrbactin compound can lead to accumulation of LC3-II protein in cells, indicating the onset of autophagy. In some embodiments, syrbactin-induced autophagy can be prevented or reversed by administration of 3-methyladenine (3-MA).

In some embodiments, administration of a syrbactin compound leads to changes in morphology of a malignant cell. Syrbactin-induced morphological changes can be monitored by, for example, microscopic inspection of cells. As disclosed herein (Examples 3 and 12), treatment with a syrbactin compound can induce morphological changes, including rounding of cells and detachment from a surface, in malignant cell populations.

Methods of Treatment

In some embodiments, the compounds disclosed herein can be administered to a subject having a disease which can be treated by a therapy associated with proteasomal inhibition. Such therapies include, but are not limited to, inhibition of antigen presentation, anticancer therapies, antiviral therapies, anti-inflammatory therapies, and anti-bacterial therapies. Diseases or symptoms that can be treated include, but are not limited to, tissue or organ transplant rejection, autoimmune diseases, Alzheimer's disease, amyotropic lateral sclerosis, asthma, cancer, autoimmune thyroid disease, type I diabetes, ischemia-reperfusion injury, cachexia, graft rejection, hepatitis B, inflammatory bowel disease, sepsis, measles, subacute sclerosing panencephalitis (SSPE), mumps, parainfluenza, malaria, human immunodeficiency virus diseases, simian immunodeficiency viral diseases, Rous sarcoma viral diseases, cerebral ischemic injury, ischemic stroke, inflammation, inflammatory disease and tuberculosis. In addition, in embodiments of the invention, the compounds disclosed herein can be useful for immunizing a subject that can be at risk of developing an infectious disease or tumor.

In treating diseases and/or conditions as disclosed in embodiments herein, a dosage regimen and schedule of administration of a composition comprising at least a syrbactin compound can be employed. In some embodiments, the compositions disclosed herein can be administered as a series of sequential doses. The doses can be identical, or they can be provided as a series of sequentially increasing dose. Sequentially increasing doses can be provided as a linearly or exponentially increasing dose. As used herein, linearly increasing doses refers to a series of doses equal to $nd_i$ where $d_i$ is the initial dose and n is the index of the series, such that the dose series is $d_i, 2d_i, 3d_i \ldots nd_i$. By exponentially increasing doses, a series of doses equal to $x^{n-1}d_i$ wherein x>1, such that the dose series is $d_i, x^2d_i, x^3d_i, x^3d_i \ldots x^{n-1}d_i$, is meant. Thus, if x=2 each dose is twice the immediately preceding dose in the series; if x=5 each dose is five times the immediately preceding dose in the series. A series, or plurality, of doses can be 2, 3, 4, 5, 6 or more doses as is needed. In instances where the initial dose(s) administered can be at too low a dose to generate a therapeutic effect, a greater number of doses (i.e., 7, 8, 9, 10, 12, 15 or more doses) can be administered to the subject to achieve a more effective therapeutic response.

In some embodiments, the compositions disclosed herein can be administered as a continuous dose.

The quantity of composition to be administered, and the particular route and formulation, are within the skill of those in the clinical arts. Routes of administration include, but are not limited to, intravenous, intraperitoneal, intracerebrospinal, subcutaneous, intra-articular, intrasynovial, intrathecal, oral, topical or inhalation routes. In preferred embodiments of the invention, intravenous or intraperitoneal administration of composition is conducted.

For the prevention or treatment of disease, the appropriate dosage of composition will depend on the type of disease to be treated, the severity and course of the disease, whether the composition is administered for preventive or therapeutic purposes, previous therapy, the patient's clinical history and response to the other previous treatment, and the discretion of the attending physician. The composition is suitably administered to a subject at one time or over a series of treatments. In a combination therapy regimen, the compositions disclosed herein can be administered in a therapeutically effective or synergistic amount. As used herein, a therapeutically effective amount is such that co-administration of a composition disclosed herein, alone or in combination with one or more other therapeutic agents results in reduction or inhibition of the targeting disease or condition. A therapeutically synergistic amount is that amount of syrbactin composition and one or more other therapeutic agents necessary to synergistically or significantly reduce or eliminate conditions or symptoms associated with a particular disease.

Doses are administered to a subject depending on the mass of the subject and can range from approximately 0.5 mg/kg to approximately 20 mg/kg. The dose will depend on whether, for example, the composition is provided as one or more separate administrations, or by continuous infusion. If provided as separate administrations, after an initial dose, further doses can be administered at a frequency of 1 hour, 4 hours, 6 hours, 12 hours, 24 hours, 48 hours, 72 hours or weekly. Duration of administration can be from about 3 up to about 16 weeks.

Screening Methods

In embodiments of the invention, methods to screen the compounds disclosed herein or analogs or derivatives thereof, including syringolins, glidobactins and derivatives or analogs thereof. The methods can include any means of detecting a 12-member ring having a 3,4 double bond. The methods can further include any means of detecting proteasome inhibition and/or apoptosis in cells.

In embodiments of the invention, a method to screen a compound for inhibition of proteasomal activity is provided, comprising the steps of: administering the compound to a population of neoplastic cells; and assaying the cells for inhibition of proteasomal activity, wherein inhibition of proteasomal activity is indicative of the effectiveness of the compound. In some embodiments, the step of assaying the cells comprises assaying the inhibition at least one type of proteasomal activity selected from the following group: chymotrypsin-like activity, trypsin-like activity and caspase-like activity. In some embodiments, the step of assaying the cells comprises assaying the accumulation of ubiquitinated proteins.

In embodiments of the invention, a method to screen a compound for the ability to induce apoptosis is provided, comprising the steps of: administering the compound to a population of neoplastic cells; and assaying the cells for induction of apoptotic activity, wherein induction of apoptotic activity is indicative of the effectiveness of the compound. In some embodiments, the step of assaying the cells for induction of apoptotic activity comprises assaying total protein level of p53. In some embodiments, the step of assaying the cells for induction of apoptotic activity comprises assaying cleavage of poly (ADP-ribose) polymerase (PARP). In some embodiments, the step of assaying the cells for induction of apoptotic activity comprises assaying extraversion of phosphatidyl serine.

In embodiments of the invention, a method to screen a compound for the ability to induce autophagy is provided, comprising the steps of: administering the compound to a population of neoplastic cells; and assaying the cells for induction of autophagy, wherein induction of autophagy is indicative of the effectiveness of the compound. In some embodiments, the step of assaying the cells for induction of autophagy comprises assaying levels of microtubule-associated protein 1 light chain 3 (LC3). In some embodiments, the LC3 protein is LC3-II protein.

In embodiments of the invention, a method to screen a syringolin or glidobactin compound is provided, comprising confirming the presence of a 12-member ring having a 3,4 double bond; and assaying the compound for inhibition of proteasomal activity and/or apoptosis and/or the ability to induce autophagy.

In some embodiments of the invention, a method to screen a compound for the ability to bind a proteasome is provided, comprising the steps of: administering the compound to a population of cells; lysing the cells, crystallizing proteins out of the cell lysate, and determining whether the compound co-crystallizes with the 20S proteasome, wherein co-crystallization is indicative of the ability of the compound to bind the proteasome.

Pharmaceutically-Acceptable Salts

In embodiments of the invention, pharmaceutically-acceptable salts of compounds are included. The term "pharmaceutically-acceptable salts" includes salts commonly used to form alkali metal salts and to form addition salts of free acids or free bases. The nature of the salt is not critical, provided that it is pharmaceutically-acceptable. Suitable pharmaceutically-acceptable acid addition salts of the compounds can be prepared from an inorganic acid or from an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids, examples of which are formic, acetic, adipic, butylic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxyethanesulfonic, nicotinic, 2-naphthalenesulfonic, oxalic, palmoic, pectinic, persulfuric, 2-phenylpropionic, picric, pivalic, propionic, succinic, tartaric, thiocyanic, mesylic, undecanoic, stearic, algenic, β-hydroxybutylic, salicylic, galactaric and galacturonic acid. Suitable pharmaceutically-acceptable base addition salts of the compounds include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts can be prepared by conventional means from the corresponding compound of the invention by reacting, for example, the appropriate acid or base with the compound. When a basic group and an acid group are present in the same molecule, the compounds can also form internal salts.

Combinations

In embodiments of the invention, the compounds of the invention can be administered as the sole active agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound disclosed herein with at least one other pharmaceutical agent, is intended to embrace administration of each agent in a sequential manner in a regimen that will provide beneficial effects of the drug combination, and is intended as well to embrace co-administration of these agents in a substantially simultaneous manner, such as in a single dose having a fixed ratio of these active agents or in multiple, separate doses for each agent.

Specifically, the administration of the compounds disclosed herein can be in conjunction with additional therapies known to those skilled in the art in the prevention or treatment of neoplastic disease, such as with radiation therapy or with cytostatic or cytotoxic agents.

Standard treatment of primary tumors can consist of surgical excision followed by either radiation or intravenously (IV) administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

A large number of antineoplastic agents is available in commercial use, in clinical evaluation and in pre-clinical development, which can be selected for treatment of neoplastic disease by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which can be used in combination with embodiments of the invention disclosed herein comprises antimetabolite-type/thymidilate synthase inhibitor antineoplastic agents. Suitable antimetabolite antineoplastic agents can be selected from, but are not limited to, the group consisting of 5-FU-fibrinogen, acanthifolic acid, aminothiadiazole, brequinar sodium, cammofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which can be used in combination with embodiments of the invention disclosed herein comprises alkylating-type antineoplastic agents. Suitable alkylating-type antineoplastic agents can be selected from, but not limited to, the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumitomo DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unfitted G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which can be used in combination with embodiments of the invention disclosed herein comprises antibiotic-type antineoplastic agents. Suitable antibiotic-type antineoplastic agents can be selected from, but are not limited to, the group consisting of Taiho 4181-A, aclarubicin, actinomycin D, actinoplanone, Erbamont ADR-456, aeroplysinin derivative, Ajinomoto AN-201-1, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, crbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, zorubicin, peptide boronates (e.g. bortezomib), α'β'-epoxyketones (e.g. epoxomoxin), β-lactones (e.g. salinosporamide A, salinosporamide B, fluorosalinosporamide, lactacystin), cinnabaramide A, cinnabaramide B, cinnabaramide C, belactosines (e.g. homobelactosin C), fellutamide B, TMC-95A, PS-519, omuralide, and antiprotealide 'Salinosporamide-Omularide Hybrid.'

A fourth family of antineoplastic agents which can be used in combination with embodiments of the invention disclosed herein comprises a miscellaneous family of antineoplastic agents, including, but not limited to, tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes C1H-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine; cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, with anolides and Yamanouchi YM-534.

In some embodiments, the compounds disclosed herein can be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, RAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alpha, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alpha, interferon alpha, natural, interferon alpha-2, interferon alpha-2a, interferon alpha-2b, interferon alpha-N1, interferon alpha-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alpha-2b, pentosan polysulfate sodium, pentostatin, picibanil, pirarubicin, rabbit antithymocyte polyclonal antibody, polyethylene glycol interferon alpha-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alpha, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17-immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb) (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), valspodar, or proteasome inhibitors, including, but not limited to, peptide aldehydes (such as, for example, calpain inhibitor I/II, MG132), peptide boronates (such as, for example, Velcade/bortezomib, CEP-18770), β-lactones (such as, for example, lactacystin, Salinosporamide A/B, NPI-0052), peptide vinyl sulfones (such as, for example, NLVS, YLVS, ZLVS), and peptide epoxylketones (such as, for example, epoxomycin, TMC, carfilzomib).

In some embodiments, the compounds disclosed herein can be used in co-therapies with other agents, such as other kinase inhibitors including p38 inhibitors and CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors, and anti-inflammatories.

Synergistic Combinations

In some embodiments, the combinations disclosed herein can comprise a therapeutically effective amount that provides additive or synergistic therapeutic effects. The combination of at least one proteasome inhibiting compound plus a second agent described herein can be useful for synergistically enhancing a therapeutic response, such as, for example, inducing apoptosis in malignant cells, reducing tumor size, or providing chemoprevention. Such combinations can be administered directly to a subject for preventing further growth of an existing tumor, enhancing tumor regression, inhibiting tumor recurrence, or inhibiting tumor metastasis. The combinations can be provided to the subject as immunological or pharmaceutical compositions. In addition, components of the synergistic combination can be provided to the subject simultaneously or sequentially, in any order.

In some embodiments, synergistic combinations of compounds, and methods of using the same, can prevent or inhibit the growth of a tumor or enhance the regression of a tumor, for instance by any measurable amount. The term "inhibit" does not require absolute inhibition. Similarly, the term "prevent" does not require absolute prevention. Inhibiting the growth of a tumor or enhancing the regression of a tumor includes reducing the size of an existing tumor. Preventing the growth of a tumor includes preventing the development of a primary tumor or preventing further growth of an existing tumor. Reducing the size of a tumor includes reducing the size of a tumor by a measurable amount, for example at least 5%, at least 10%, at least 20%, at least 30%, at least 40%, at least 50%, at least 60%, at least 70%, at least 80%, at least 85%, at least 90%, at least 95%, at least 99%, or 100%.

Pharmaceutical Compositions

Pharmaceutical compositions that include one or more proteasome-inhibiting compounds disclosed herein, can be formulated with an appropriate solid or liquid carrier, depending on the particular mode of administration chosen. The pharmaceutically acceptable carriers and excipients useful in this disclosure are conventional. For example, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for example, other proteins, such as human serum albumin or plasma preparations. Optionally, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

An effective amount of a proteasome-inhibiting compound can be administered in a single dose, or in several doses, for example daily, during a course of treatment. The amount of active compound(s) administered is dependent on the compound being used, the subject being treated, the severity of the affliction, and the manner of administration, and is best left to the judgment of a prescribing clinician. An effective amount of a compound can be administered prior to, simultaneously with, or following treatment of a disease for which the proteasome is a therapeutic target. Within these bounds, the formulation to be administered will contain a quantity of the active component(s) in amounts effective to achieve the desired effect in the subject being treated. For example, an effective amount of compound is one that measurably reduces the recurrence of a tumor.

Site-specific administration of the disclosed compounds can be used, for instance by applying a compound to a region of tissue where therapeutic results are desired. For example, compound can be delivered to a site from which a tumor has been removed or near a region of tissue from which a tumor has been removed. In some embodiments, sustained intra-tumoral (or near-tumoral) release of the pharmaceutical preparation that comprises a therapeutically effective amount of a proteasome-inhibiting compound can be beneficial. Slow-release formulations are known to those of ordinary skill in the art. By way of example, polymers such as bis(p-carboxyphenoxy)propane-sebacic-acid or lecithin suspensions can be used to provide sustained intra-tumoral release.

Kits

Any of the compositions described herein can be assembled together in a kit. In a non-limiting example, a composition comprising a compound as disclosed herein can be provided in a kit alone, or in combination with additional agents or reagents for treating a disease or condition, such as cancer. However, these components are not meant to be limiting. In some embodiments, the kits will provide a suitable container means for storing and dispensing the agents or reagents.

Where components of the kit are provided in one or more liquid solutions, the liquid solution is an aqueous solution, with a sterile aqueous solution being particularly preferred. The compositions can also be formulated as a deliverable and/or injectable composition. In such embodiments, the container means can itself be a syringe, pipette, and/or other such apparatus, from which the formulation can be delivered or injected into a subject, and/or even applied to and/or mixed with the other components of the kit. In some embodiments, the components of the kit can be provided as dried powder(s). When components (e.g., reagents) are provided as a dry powder, the powder can be reconstituted by the addition of a suitable solvent. It is envisioned that the solvent can also be provided in another container means.

The container means will generally include at least one vial, test tube, flask, bottle, syringe and/or other container means, into which a composition comprising a syrbactin compound and optionally one or more agents can be placed. The kit can also comprise a second container means for containing a sterile, pharmaceutically acceptable buffer and/or other diluent. In some embodiments, the kit can also include a means for containing the materials for practicing the methods disclosed herein, and any other reagent containers in close confinement for commercial sale. Such containers can include, for example, injection or blow-molded plastic containers into which the desired vials are retained. Irrespective of the number or type of containers, the kit(s) of the invention can also comprise, or be packaged with, an instrument for assisting with the injection/administration of the bicistronic vector comprising: one or more prophylactic or therapeutic agents and one or more agents that interfere with the expression of biological response modifiers, within the body of a subject. Such an instrument can be, for example, but not limited to, a syringe, pump and/or any such medically approved delivery vehicle.

Having described the invention in detail, it will be apparent that modifications, variations, and equivalent embodiments are possible without departing the scope of the invention defined in the appended claims. Furthermore, it should be appreciated that all examples in the instant disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the instant disclosure, appreciate that many changes can be made in the specific embodiments that are disclosed and still obtain a like or similar result without departing from the spirit and scope of the invention.

Example 1

Purification of Syringolin A

*Pseudomonas syringae* pv. *syringae* strain B 301D-R was grown as described (Wäspi or al. 1999. *Microbial. Res.* 154: 89-93; Mo and Gross. 1991. *J. Bacterial.* 173:5784-5792; Gross. 1985. *J. Appl. Bacterial.* 58:167-174, each of which is incorporated herein by reference in its entirety). For syringolin production, 3 ml of SRMAF medium (1% D-glucose, 0.1% fructose, 100 mM arbutin, 0.4% L-histidine, 0.8 mM $MgSO_4$, 10 mM $FeCl_3$, 0.8 mM potassium phosphate, pH 7) were inoculated with a colony picked from a 2×YT agar plate and incubated on a rotary shaker (250 rpm; Kühner, Basel, Switzerland) overnight at 25° C. Two hundred ml of fresh SRMAF medium were inoculated with 2 ml of the overnight culture and incubated for 5 to 8 days at 25° C. without shaking. Two hundred ml of conditioned medium were centrifuged at 12,000×g for 20 minutes and sterile-filtered (0.22 μm pore size). One liter of conditioned medium was collected from multiple cultures, lyophilized, dissolved in 100 ml distilled water, and loaded on an Amberlite XAD 16 column (2.6×40 cm; Rohm and Haas, Philadelphia, Pa.) equilibrated with water. After washing with 300 ml water and 300 ml 20% (v/v) methanol, bound compounds were eluted with 400 ml 70% (v/v) 2-propanol. The eluate was evaporated to dryness on a Rotavapor-R evaporator (Büchi, Flawil, Switzerland) at 50° C. and dissolved in 25 ml distilled water. After addition of trifluoroacetic acid to a final concentration of 0.06%, 5-ml aliquots were isocratically separated by reverse-phase-HPLC on a Nucleosil 100 7 C18 250/10 column (Macherey-Nagel, Düren, Germany) with 20% (v/v) acetonitrile and 0.06% (v/v) trifluoroacetic acid in water using a flow rate of 5 ml/min. Absorption was monitored at 206 nm. The peak eluting after approximately 11 minutes under these conditions was collected and lyophilized. Its identity is verified using a standard, which itself was verified using mass spectrometry.

Example 2

Purification of Glidobactin

Glidobactin was extracted as previously described (Oka, et al. 1998. *J. Antibiot.* 41:1331-1337, which is incorporated herein by reference in its entirety). Alternatively, glidobactin was extracted from bacterial cultures grown on CY (3.00 g/L bactotryptone, 1.36 g/L $CaCl_2 \times 2H_2O$, 1.00 g/L yeast extract) agar plates as described (Schellenberg, et al. 2007. *Env. Microbiol.* 7:1640-1650, which is incorporated herein by reference in its entirety). For a typical extraction, each of 12 plates (9 cm diameter) was inoculated with nine 10-microliter aliquots of bacterial cultures grown over night in the absence (wild type) or presence (insertion mutants) of 10 μg/mL tetracyline, whereby one droplet was placed at the center and 8 droplets equidistantly at the periphery of a plate. Plates were incubated for 10 hours at 37° C. and then for ten days at room temperature. The contents of the plates were then cut into small pieces and transferred to a flask to which 35 mL methanol was added per plate. The suspension was shaken for 2 hours at room temperature. The extract was decanted into a fresh flask, passed through a 0.2-μm filter unit, 10-fold concentrated in a rotary evaporator at 35-40° C., and subjected to HPLC analysis. HPLC analysis was performed as described (Titus and Roundy. 1990. *J. Ind. Microbiol.* 6:215-218, which is incorporated herein by reference in its entirety) with minor modifications. Ten-fold concentrated methanol extract was filtered through Millex GP filter units (0.22 μm pore size; Millipore, Molsheim, France). Twenty μL (for analytical runs) or 200 μL (for preparative runs) filtrate was injected into a 250 mm×4.6 mm Hypersil ODS 5 μm column (Dr. Maisch GmbH, Ammerbuch, Germany) which was connected to a Gynkotek model P580 HPG HPLC pump (Dionex, Synnyvale, Calif., U.S.A.) and a UVIS 204 detector (Linear Instruments Corp., Reno, Nev., U.S.A.). Equilibration of the column and isocratic separation of the extract were performed with a 75% methanol: 25% water solution at a flow rate of 1 mL/min. Absorption at 260 nm was monitored with a Millipore CR112 recorder. Under these conditions, the approximate retention times of peak 1 (glidobactin A) and peak 2 were 10.5 and 12.0 min, respectively. Concentrations of GlbA solutions were determined by measuring the absorption at 261 nm in methanol using an extinction coefficient of 35,000 $M^{-1}cm^{-1}$ (Oka, et al. 1998. *J. Antibiot.* 41:1331-1337, which is incorporated herein by reference in its entirety).

Example 3

Anti-Proliferative Effects and Morphological Changes in Syringolin A-Treated Neuroblastoma and Ovarian Cancer Cells To examine the effect of syringolin A on the proliferation rate of mammalian cancer cells, syringolin A was first purified from the conditioned medium of cultures of *Pseudomonas syringae* pv. *syringae* as previously described. The purity of syringolin A was confirmed by reverse-phase HPLC using a syringolin A standard, which itself had been previously purified in an identical manner and verified by mass spectrometry. Lyophilized syringolin A was dissolved in ultrapure distilled water (Invitrogen, Carlsbad, Calif.) at a concentration of 2.5 mM (stock solution), sterile-filtered with a 0.2 μm filter, aliquoted into sterile tubes and was stored frozen at −80° C. Aliquots were thawed and used for cell culture studies at different concentrations as indicated below.

The mammalian cell lines used to test the effects of syringolin A were human neuroblastoma (NB) cells with either wild type p53 (line SK-N-SH, provided by the American Type Culture Collection [ATCC], Manassas, Va.; Davidoff, et al. 1992. *Oncogene* 7:127-133; McKenzie, et al. 1999. *Clin. Cancer Res.* 5:4199-4207; Tweddle, et al. 2001. *Am. J. Pathol.* 158:2067-2077), mutant p53 (line LAN-1, cysteine to stop codon at residue 182, provided by Dr. Robert Seeger, University of California, Los Angeles, Calif.; Davidoff, et al. 1992. *Oncogene* 7:127-133; Tweddle, et al. 2001. *Cancer Res.* 61:8-13; Tweddle, et al. 2003. *Cancer Lett.* 197:93-98), or human ovarian cancer cells (line SKOV3, provided by Dr.

Bonnie Warn-Cramer, Cancer Research Center of Hawaii). NB cells were maintained in RPMI 1640 (Biosource, Rockville, Md.) containing 10% (v/v) heat-inactivated fetal bovine serum (FBS) (Invitrogen, Carlsbad, Calif.), penicillin (100 IU/ml), and streptomycin (100 µg/ml) as previously described (Wallick, et al. 2005. Oncogene 24:5606-5618). SKOV3 cells were maintained in McCoy's 5A with L-glutamine (Mediatech Inc., Herndon, Va.) and containing 10% (v/v) heat-inactivated fetal bovine serum (PBS) (Invitrogen, Carlsbad, Calif.) and gentamicin (100 µL/mL). Cells were seeded 18-24 hours before GlbA or SylA treatment and analyzed after 24 and/or 48 hours. Cell numbers were determined using a haemacytometer in the presence of trypan blue (Fisher Scientific, Pittsburgh, Pa.).

To then test the effects of syringolin A on proliferation, cells at $0.25$-$0.5 \times 10^5$ cells per ml were seeded in 96-well microtiter plates containing 100 µl of culture medium per well. After 24 hours, syringolin A was added to wells to a final concentration of 0.5 µm to 100 µm. Syringolin was not added to parallel samples of control cells. Cells were incubated for 48 hours, photographed, and the viability of cells (calculated as a percentage of control cell counts) was determined using the sulphorhodamine B (SRB) assay as previously reported (Skehan, et al. 1990. J. Natl. Cancer Inst. 82:1107-1112, which is incorporated herein by reference in its entirety). In brief, cell culture medium was removed from the microtiter plate and adherent cells were fixed with 10% (w/v) trichloracetic acid (TCA) for 30 minutes at room temperature. Following four washes with tap water, 100 µl of SRB (Sigma Chemical Co., St. Louis, Mo.) (0.4 g/100 ml 1% [v/v] glacial acetic acid in water) was added and the plate was then incubated for 30 minutes at room temperature, and rinsed four times with 3% (v/v) glacial acetic acid. After addition of 200 µl of 10 mM Tris base (not pH adjusted) to each well, the plate was incubated on an orbital shaker for 30 minutes until the SRB was uniformly dissolved. The absorption at a wavelength of 560 nm was read using an HTS 7000 Plus Bioassay Reader or a Victor 3, 1420 Multilabel Counter (PerkinElmer, Inc. Boston, Mass.). To record cell morphology with and without syringolin treatment, photomicrographs were taken of cells in 12-well plates or 96-well plates, in the presence or absence of 25 µM syringolin A, using a Nikon Diaphot inverted microscope (Nikon Corp., Tokyo, Japan) and a Carl Zeiss Axiovert 200M inverted microscope (Carl Zeiss, Goettingen, Germany), both equipped with a digital camera and computer software for image processing. Power of magnification for SK-N-SH, LAN-1, and SKOV3 cells was 20×, and for Rat-1 cells was 10×.

As illustrated in FIG. 2, syringolin A addition reduced the cell viability of both cell lines SK-N-SH (FIG. 2A) and LAN-1 (FIG. 2D) in a dose-dependent manner. The $IC_{50}$ (inhibitor concentration at which cell proliferation rate is reduced by 50% relative to control) for both syringolin A-treated NB cell lines was between 20 and 25 µm. Concomitant with its inhibitory effects, syringolin A also induced significant morphological changes in both SK-N-SH cells (FIG. 2C) and LAN-1 cells (FIG. 2J). In contrast with their typical triangular cell shape (FIGS. 2B and E), nearly all cells now appeared round and were detached from the cell culture dish (floater cells) 48 hours after treatment with syringolin A (FIGS. 2C and F). The detachment was more pronounced in SK-N-SH cells (black arrows). The observed morphological changes are characteristic for cells that undergo apoptosis.

To establish that the anti-proliferative effect of syringolin A is not specific to NB cells, identical experiments were performed with p53-deficient ovarian cancer cells SKOV3 (Cancer Research Center of Hawaii) and immortalized Rat-1 fibroblasts cells. SKOV3 cells, which are p53-deficient and overexpress activated protein kinase Akt/PKB (Wang, et al. 2005. Oncogene 24:3574-3582, which is incorporated herein by reference in its entirety), were maintained in McCoys 5 A medium (Sigma Chemical Co., St. Louis, Mo.) supplemented with 5% (v/v) FBS and 100 µg/ml gentamicin. Immortalized fibroblast cells Rat-1 (Cancer Research Center of Hawaii, HI) were maintained in Dulbecco's modified Eagle's medium (DMEM) (Sigma Chemical Co., St. Louis, Mo.) supplemented with 10% (v/v) FBS (Goldberg & Lau. 1993. Biochem. J. 295:735-742, which is incorporated herein by reference in its entirety). Syringolin A reduced the cell proliferation rate of SKOV3 cells (FIG. 2G) and Rat-1 cells (FIG. 23) in a dose-dependent manner, thus indicating that syringolin A is also active in other types of mammalian cell lines at comparable concentrations. Syringolin A also affected the cell morphology of both SKOV3 cells and Rat-1 cells; however, neither cell detachment nor floating cells were observed (FIGS. 2I and L).

Example 4

Syringolin A Treatment Leads to Rapid Increase in p53 Protein Levels in Cancer Cells, Indicating an Apoptotic Response The mechanism by which syringolin A inhibits cell proliferation was demonstrated in SK-N-SH cells, which have a strong apoptotic response in the presence of syringolin A (FIG. 2C). Because p53 is a key regulator and mediator of apoptosis, the total protein levels of p53 in the p53-wild type cell line SK-N-SH were measured after treatment of cells with syringolin A. As a control, the p53-deficient cell line SKOV3 was tested in parallel. Cells at a concentration of $1.0 \times 10^5$ cells per ml were first seeded in six-well plates containing 2 ml of culture medium per well. After 24 hours, 16 µl of syringolin A (20 µM final concentration) or an equal volume of sterile water (control) was added per well. Cells were incubated for 0, 24, and 48 hours, harvested, and lysed in radioimmuno-precipitation assay (RIPA) buffer (20 mM Tris-HCl, pH 7.5, 0.1% sodium lauryl sulphate, 0.5% sodium deoxycholate, 135 mM NaCl, 1% Triton X-100, 10% glycerol, 2 mM EDTA), supplemented with a protease inhibitor cocktail (Roche Molecular Biochemicals, Indianapolis, Ind.) and phosphatase inhibitors sodium fluoride (NaF; 20 mM) and sodium vanadate ($Na_3VO_4$; 0.27 mM). The total protein concentration was determined using the protein assay dye reagent from Bio-Rad Laboratories (Hercules, Calif.) and bovine serum albumin (BSA) as a standard. Cell lysates in Laemmli sample buffer (Bio-Rad Laboratories, Hercules, Calif.) containing 5% (v/v) β-mercaptoethanol were boiled for 5 minutes, and equal amounts of total protein were analyzed by 10% sodium dodecyl sulphate-polyacrylamide gel electrophoresis (SDS-PAGE) and Western blotting using PVDF membranes. p53 was detected in Western blotting with mouse monoclonal anti-p53 (sc-126) (diluted 1:250) from Santa Cruz Biotechnology (Santa Cruz, Calif.). Actin was also detected as a loading control using mouse monoclonal anti-β-actin (A5316) (diluted 1:1000) from Sigma Chemical Co. (St. Louis, Mo.). Alternatively, lysates were blotted with rabbit monoclonal anti-caspase-3 (#9665) (diluted 1:1000) or rabbit polyclonal anti-Akt (#9272) (diluted 1:1000), both from Cell Signalling Technology, Inc. (Beverly, Mass.) to test for levels of procaspase-3 and Akt/PKB. Secondary anti-mouse (diluted 1:5000) and anti-rabbit (diluted 1:5000) antibodies coupled to horseradish peroxidase (HRP) were from Amersham Biosciences (Piscataway, N.J.). Proteins were detected using the ECL Plus reagents (Amersham Biosciences, Piscataway, N.J.) and Kodak BioMax XAR film (Fisher Scientific, Pittsburgh, Pa.). The results are representative of three (p53, procaspase-3) or four (Akt/PKB) independent experiments.

In syringolin. A-treated SK-N-SH cells, p53 levels rapidly increased as early as 24 hours after treatment (FIG. 3A). Levels of p53 declined after 48 hours, indicating that the induction of p53 is an early response and precedes the onset of apoptosis. A second p53-reactive band at 40 kDa (p40) appeared and was previously observed in SK-N-SH cells (Heiligtag, et al. 2002. *Cell Death Differ.* 9:1017-1025, which is incorporated herein by reference in its entirety). As expected, p53 was not detected in p53-deficient SKOV3 cells (FIG. 3B). Equal amounts of total protein were loaded in all experiments (10 µg per lane) as judged by protein assay using the protein dye reagent from Bio-Rad. Together, these data indicate that syringolin A activates p53 in SK-N-H cells.

Figure 3:
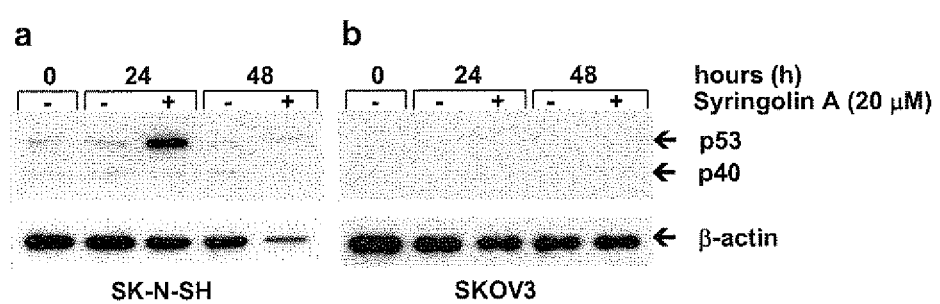
FIG. 3 is a Western blot showing an increase in p53 levels in mammalian cancer cells after treatment with syringolin A.
Figure 4:
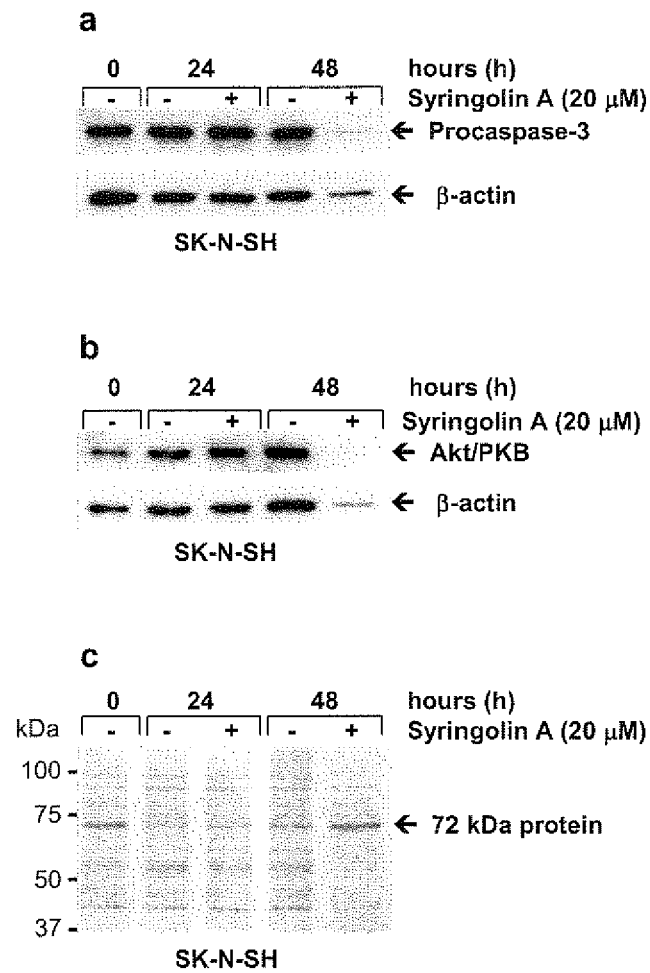
FIG. 4 includes Western blots (A,B) and a Coomassie-stained gel (C) which show a decrease in general protein synthesis, as indicated by decreasing amounts of β-actin, procaspase-3, and protein kinase Akt/PKB (A,B) and of general proteins (C) following treatment of mammalian cancer cells with syringolin A.

The observed decrease of p53 in syringolin A-treated samples at 48 hours may in part be the result of a general shutdown of protein synthesis, as Western blotting indicated that the levels of several other proteins including β-actin, procaspase-3 and protein kinase Akt/PKB decreased in a similar manner despite the loading of equal amounts of total protein in each lane (FIGS. 3 and 4). This observation was reproduced in replicate experiments (n=3). Visualization of protein bands, by the Coomassie blue membrane staining method, further revealed that several proteins are down-regulated in syringolin A-treated cells after 48 hours (FIG. 4C), with the exception of one protein at approximately 72 kDa, which was strongly up-regulated (black arrow) (n=3). Because the same amount of total protein (10 µg) was loaded in each lane, it is possible that the observed general decrease in proteins is compensated by the strong increase of the 72 kDa protein, thus resulting in a protein sample that overall contains the same amount of total protein. Therefore, the differences observed for antibody staining at 48 hours are the result of syringolin A treatment and not from differences in loading.

Example 5

Figure 5:
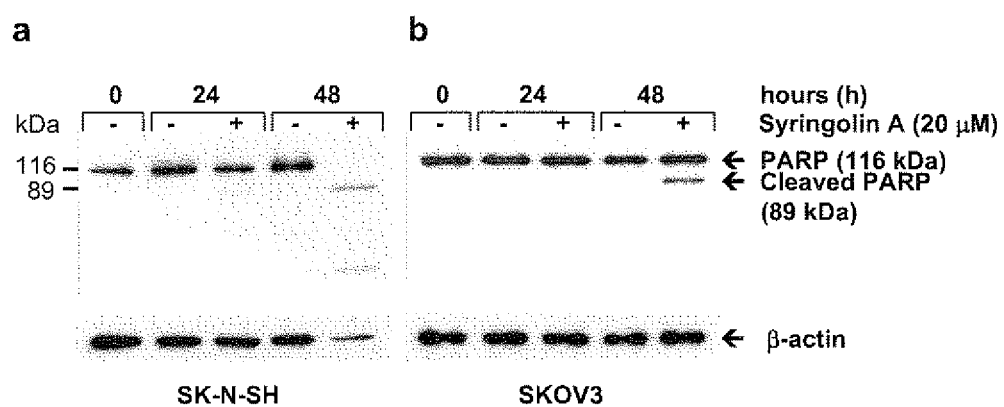
FIG. 5 includes Western blots that reveal cleavage of poly ADP-ribose polymerase (PARP), a hallmark of apoptosis, in mammalian cancer cells following treatment with syringolin A.

Syringolin A Treatment of Mammalian Cancer Cells Results in PARP Cleavage, a Common Apoptotic Response The induction of an apoptotic response in cancer cells by the addition of syringolin A was verified by monitoring the cleavage of poly (ADP-ribose) polymerase (PARP), a common response during apoptosis. SK-N-SH cells were cultured in the presence or absence of 20 µM syringolin A for 0, 24 and 48 hours, and cell lysates were then generated as described in Example 4 and probed for the presence of PARP by Western blotting using rabbit polyclonal anti-PARP (#9542) (diluted 1:1000) and the HRP-linked anti-rabbit secondary antibody described in Example 4. The results were representative of four independent experiments. As shown in FIG. 5A, noncleaved PARP (116 kDa) was detected in cell lysates of untreated cells after 0, 24 and 48 hours, whereas cleaved PARP (89 kDa) and reduced levels of the noncleaved PARP were observed in syringolin A-treated cells after 24 hours. The treatment of cells for 48 hours further increased the levels of cleaved PARP, whereas noncleaved PARP disappeared. In a similar manner, syringolin A induced PARP cleavage in SKOV3 cells, but noncleaved PARP was still detected 48 hours after treatment (FIG. 5B). These results indicated that syringolin A induces apoptosis-associated PARP cleavage in both SK-N-SH and SKOV3 cells.

Example 6

Induction of Apoptosis-Associated Extraversion of Phosphatidyl Serine in Syringolin A-Treated Mammalian Cancer Cells To further demonstrate that syringolin A can induce apoptosis, SK-N-SH cells were analyzed by flow cytometry using the annexin V assay, a sensitive method used to detect apoptotic cells. Annexin V detects phosphatidyl serine, an intracellular cell membrane component which is extraverted in apoptotic cells and displayed on the cell surface. SK-N-SH cells at a concentration of $1.0 \times 10^5$ cells per ml were seeded in 12-well plates containing 1 ml of culture medium per well. After 24 hours, 10 µl of syringolin A (25 µM final concentration) or an equal volume of sterile water (control) was added per well. Cells were incubated for 48 hours, trypsinized, washed twice in phosphate-buffered saline (PBS) and were counted; $1\text{-}2 \times 10^5$ cells suspended in 0.1 ml of 1× assay buffer per vial according to the manufacturer's instructions (BD Biosciences, Palo Alto, Calif.). Cells were stained with annexin V-FITC (5 µl) for 15 minutes in the dark, at room temperature. Assay buffer (0.4 ml) was added, and 5000 cells were analyzed using a FACScan flow cytometer (Becton Dickinson, San Jose, Calif.). The CELLQUEST program was used for data analysis.

Figure 6:
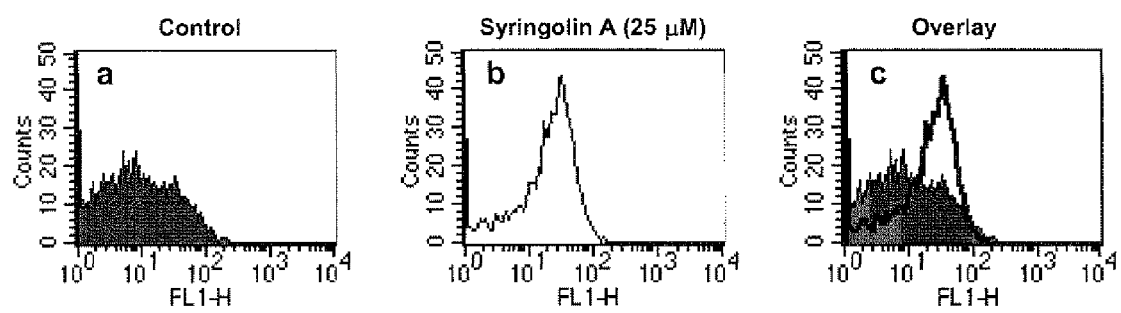
FIG. 6 includes flow cytometry histograms showing the binding of apoptotic cell marker Annexin V to mammalian cancer cells either treated (B) or not treated (A) with syringolin A.

As shown in FIG. 6, SK-N-SH cells treated with 25 µM syringolin A for 48 hours strongly bound annexin V (FIG. 6B), whereas cells in the absence of syringolin A (FIG. 6A) did not bind annexin V. A shift to the right on the x-axis (FL1-H) indicates the specific binding of annexin V to the cell surface of syringolin A-treated cells, and was compared to control cells by superimposition of both histograms (n=3; overlay in FIG. 6C). This strong binding by annexin V following syringolin A treatment further confirmed that syringolin A induces apoptosis in SK-N-SH cells.

Example 7

Syringolin A Inhibits the Eukaryotic Proteasome In Vitro

The eukaryotic 20S proteasome contains three catalytic subunits (β1, β2, and (β5) conferring caspase-like, trypsin-like and chymotrypsin-like proteolytic activities, respectively (Borissenko and Groll. 2007. *Chem. Rev.* 107:687-717, which is incorporated herein by reference in its entirety). Syringolin A was tested as a proteasome inhibitor using the 20S Proteasome Assay Kit for Drug Discovery AK-740 (BIOMOL® International, Plymouth Meeting, PA, USA), which contains human erythrocyte 20S proteasomes, in a 96-well microtiter plate. The fluorogenic substrates Suc-LLVY-AMC, Boc-LRR-AMC, and Z-LLE-AMC (BIOMOL® International) were used to monitor chymotrypsin-like, trypsin-like, and caspase-like activities, respectively. A 100 µl reaction volume contained 2 µg/ml 20S proteasome, 100 µM substrate, and the desired concentrations of syringolin A in dilution buffer (50 mM Tris-HCl, pH 7.5, 25 mM KCl, 10 mM NaCl, 1 mM MgCl$_2$). Epoximicin and MG132 (BIOMOL® International) were used as test inhibitors. The release of free AMC (7-amino-4-methylcoumarin) at 37° C. was monitored with an MWGt Sirius HT fluorescence microplate reader (BIO-TEK® Instruments) equipped with a 360 nm excitation and a 460 nm emission filter. Proteolytic activities were measured as the increase in relative fluorescence units (RFU) over time (FIG. 7A-C). The fluorescence data were fitted by the least squares method using SigmaPlot version 10.0 software (Systat Software) to the equation $f=f_0+v_s t+[(v_i-v_s)/k_{obs}][1-\exp(-k_{obs}t)]$, where $v_i$ and $v_s$ are initial and final velocities, respectively, and $k_{obs}$ is the pseudo-first order association rate constant (Meng, et al. 1999. *Proc. Natl. Acad. Sci. U.S.A.* 96:10403-10408; Fenteany, et al. 1995. *Science* 268:726-731). Fittings with $R^2$ values >0.99 were usually obtained. The initial velocities ($v_i$) were determined from the time derivative of these curves and plotted versus the corresponding inhibitor concentration ([I]). Where possible, apparent $K_i'$ values (inhibitor concentration at which the initial reaction velocity [$v_i$] was 50% of the uninhibited reaction velocity [$v_0$]) were determined from these plots. Using SigmaPlot, the data were fitted to the hyperbolic equation $v_i=c+[v_0/(K_i'+[I])]$, where $v_0$ is the velocity of the control. Usually, $R^2$ values >0.98 were obtained. The rate of covalent inhibition ($k_{association}$), which equals $k_{obs}/[I]$ was calculated over the range of inhibitor concentrations given in parentheses in FIG. 7D. The pseudo-first order association rate constants $k_{obs}$ were derived from plots as shown in FIG. 7A-C. Values in FIG. 7D represent means±standard deviation.

Figure 7:
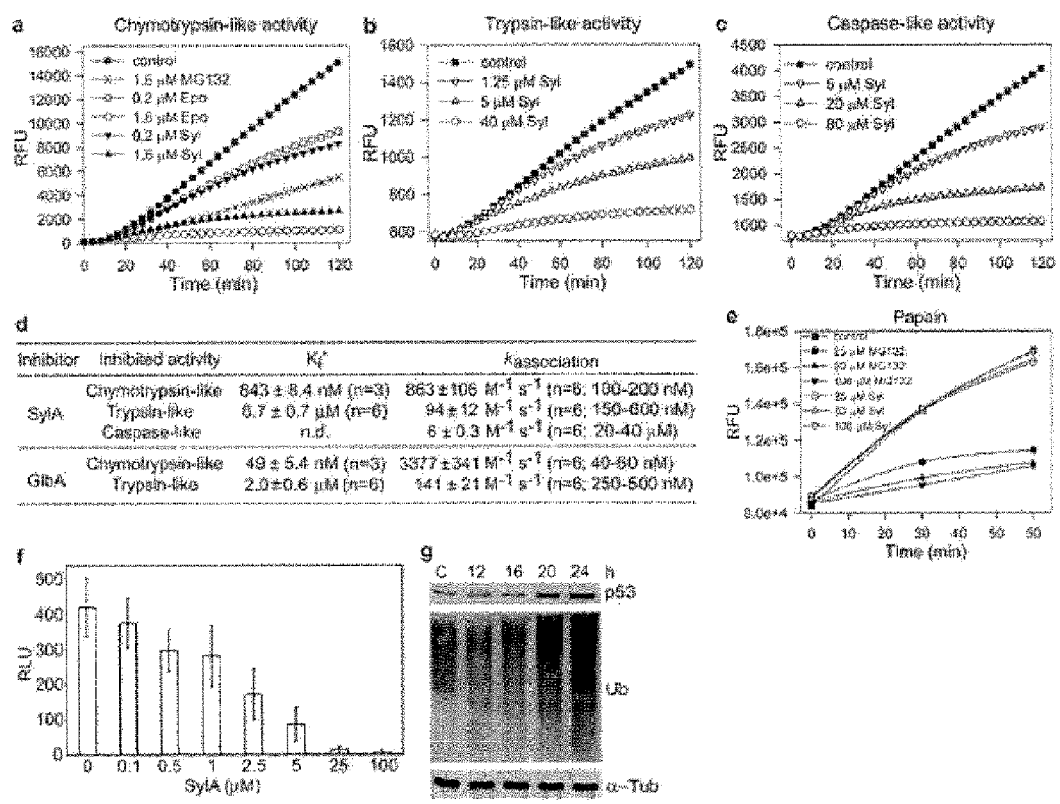
FIG. 7 includes line and bar graphs showing the specific inhibition of proteasome activity in vitro and in vivo that is caused by either syringolin A or glidobactin A, as well as Western blots that reveal an accumulation of ubiquitinated proteins indicative of proteasome inhibition.

In these experiments, syringolin A inhibited all three proteasome activities (FIG. 7A-D). In addition, proteasome activity measurements in the presence of syringolin A revealed that the proteolytic reaction velocity was not constant but diminished as a function of time. This was similar to what is observed in the presence of the irreversible proteasome inhibitor epoxomicin and in contrast to the effect of the reversible peptide aldehyde inhibitor MG-132 (FIG. 7A), indicating that syringolin A acts as an irreversible proteasome inhibitor. The chymotrypsin-like activity was found to be most sensitive to syringolin A inhibition, while higher concentrations of syringolin A were necessary to inhibit trypsin-like and caspase-like activities (FIG. 7B-D).

Figure 8:
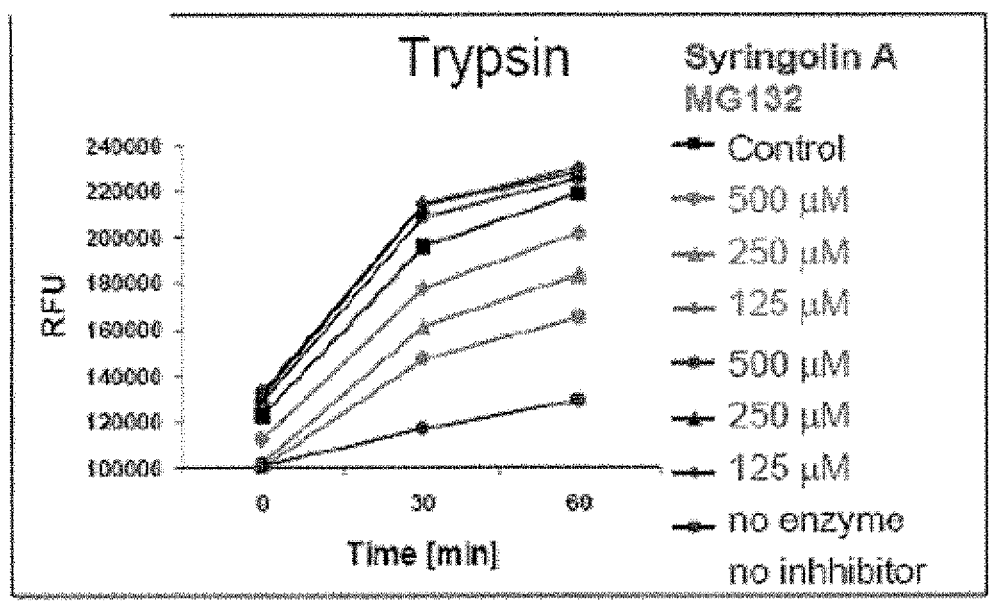
FIG. 8 is a line graph that depicts substrate cleavage profiles by trypsin in the presence of trypsin inhibitor MG132 or syringolin A, which does not inhibit trypsin activity.

To test the specificity of syringolin A inhibition of proteasome activities, bovine pancreas trypsin (Pierce) and Papaya latex papain (Sigma-Aldrich) inhibition assays with syringolin A were performed with the SensoLyte™ Green Protease Fluorometric Assay Kit (AnaSpec., San Jose, Calif., USA) according to the instructions of the manufacturer. Reaction volumes of 100 µl contained an enzyme concentration of 200 ng/ml and various amounts of test inhibitors. Protease activity was monitored at 33° C. in a FluoroCount Microplate Fluorometer (FluoroCount, Packard, Canberra, Australia) using 485 nm excitation and a 550 nm emission filters. In contrast to MG-132, which also inhibits cysteine proteases, syringolin A inhibition of the proteasome was specific since both papain (FIG. 7E) and trypsin (FIG. 8) were not affected by syringolin A, even at significantly higher concentrations (up to 500 µM).

Example 8

Syringolin A Inhibits the Eukaryotic Proteasome in Cancer Cells

Syringolin A was tested as a proteasome inhibitor in vivo in cultured mammalian cancer cells. Inhibition of proteasome activity in human SK-N-SH neuroblastoma cells was measured using the Proteasome-Glo™ cell-based luminescent assay (Promega) in solid white 96-well microtiter cell culture plates. Ten µl of syringolin A (at various concentrations) was added to each well containing SK-N-SH cells (plated at a concentration of $1.0\times10^5$ cells/ml in 90 µl well volumes 24 hours prior) and a negative control and media only control were included. Cells were incubated with 1-100 µM syringolin A for 2 hours or 24 hours, and then equilibrated to room temperature for 15 minutes before 100 µl of Proteasome-Glo reagent (containing bioluminescent substrate Suc-LLVY-aminoluciferin) was added to the cells. Luminescence (indicated as relative luminescence units [RLU]) was read after 15-30 minutes on a Dynex MLX Luminometer.

Figure 9:
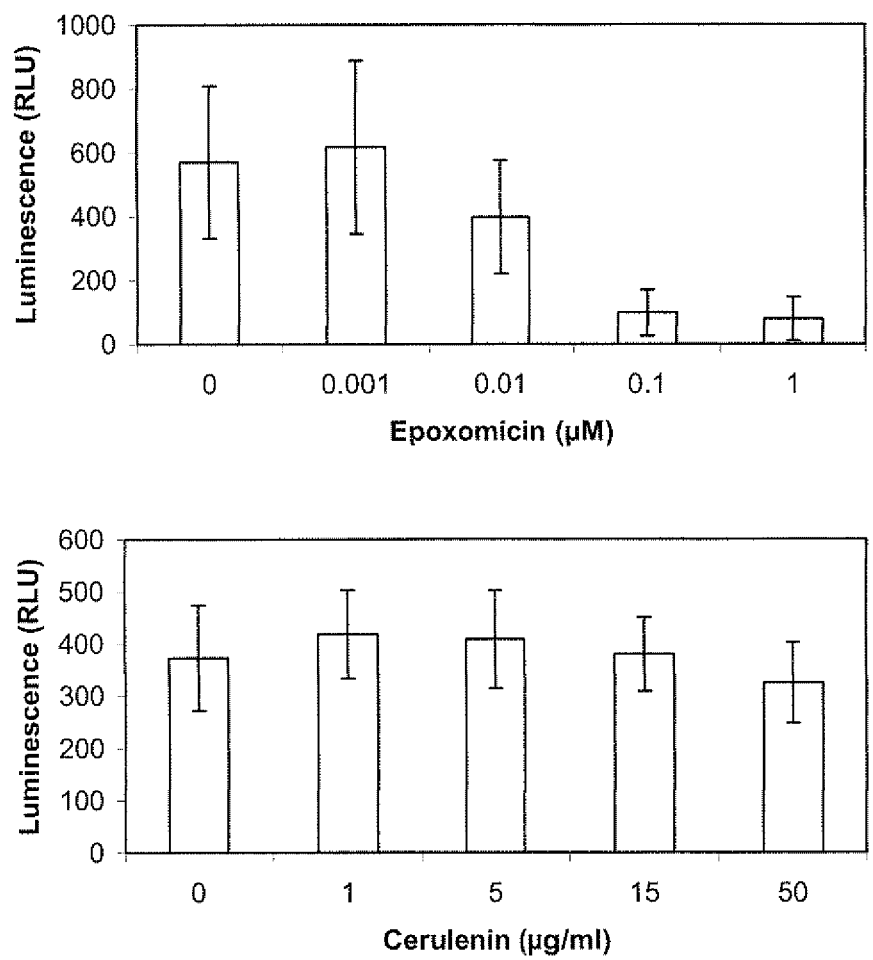
FIG. 9 is a bar graph that depicts control experiments for the experiment of FIG. 7F, which show that syringolin A inhibition of the proteasome is similar in magnitude to inhibition by the known proteasome inhibitor epoxomicin and is not a downstream consequence of induction of apoptosis, as the apoptosis inducing agent cerulenin does not significantly inhibit proteasome activity.

Incubation with syringolin A for 2 hours resulted in a dose-dependent decrease of proteasome activity (FIG. 7F). Similar results were observed with neuroblastoma cell line LAN-1, ovarian cancer cell line SKOV3, and human embryonic kidney cell line HEK-293 (not shown). Epoxomicin (0-1 µM) and cerulenin (0-50 µg/ml) were used as positive and negative proteasome inhibitor controls, respectively (FIG. 9; RLU, relative luminescence units; Means±standard deviation [n=6] are shown). Epoxomicin is an established proteasome inhibitor, while cerulenin is an apoptosis inducing agent (Geerts, et al. 2007. *Clinical Cancer Research* 13: 6312-6319; Heiligtag, et al. 2002. *Cell Death Differ.* 9:1017-1025, each of which is incorporated herein by reference in its entirety). Similar results were observed with the neuroblastoma cell line LAN-1 (not shown).

Figure 10:
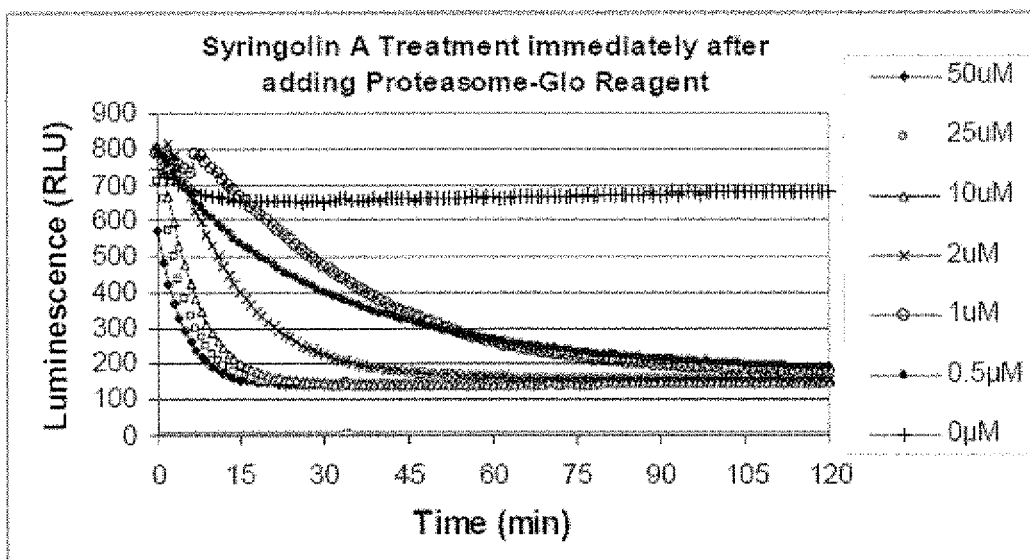
FIG. 10 is a line graph that depicts kinetic profiles of proteasome activity in vivo after treatment of mammalian cancer cells with various concentrations of syringolin. A.

To trace the kinetics of proteasome inhibition in the presence of syringolin, the same experiment was performed, but in this case, 100 µl of Proteasome-Glo reagent was added to cells first, followed by the addition of syringolin A at various concentrations, and the proteasome activity was measured over time. Syringolin A inhibited proteasome activity in a time and dose-dependent manner in the micromolar range (FIG. 10).

As inhibition of the proteasome is expected to result in increased levels of ubiquitinated proteins (Meng, et al. 1999. *Proc. Natl. Acad. Sci. U.S.A.* 96:10403-10408, which is incorporated herein by reference in its entirety), the effect of syringolin A on total ubiquitinated protein accumulation was analyzed by immunoblot analysis. To do so, SK-N-SH cells were seeded in 6-well cell culture plates at a concentration of $3.8\times10^5$ cells per ml (1.98 ml per well). After 24 hours, 20 µl of syringolin A (final concentration 25 µM) or cell culture medium (control, C) was added. For time-course experiments, cell treatments were staggered in order to process all samples at the same time after 24 hours. Cell lysates were prepared as previously reported (Wallick, et al. 2005. *Oncogene* 24:5606-5618, which is incorporated herein by reference in its entirety). Sodium dodecyl sulfate-polyacrylamide gel electrophoresis (SDS-PAGE), electro transfer to PVDF Immobilon-P membranes (Millipore) and antibody incubations were performed according to standard procedures. The primary antibodies used were rabbit whole serum ubiquitin (1:150) (U5379; Sigma), mouse monoclonal tumor suppressor protein p53 (1:250) (se-126; Santa Cruz Biotechnology), and rabbit monoclonal α-tubulin (1:1,500) (11H10; Cell Signaling Technology). Horse radish peroxidase (HRP)-conjugated anti-mouse or anti-rabbit antibodies (1:5,000) were used as secondary antibodies. Membranes were developed using the ECL Plus kit following the manufacturer's protocol (Amersham Biosciences) and exposed to Blue Lite Autorad Film (ISC BioExpress). Membranes were stripped with ECL stripping buffer (62.5 mM Tris-HCL, pH 6.7, 2% SDS, 100 mM β-mercaptoethanol) for 20 min at 55° C. and sequentially re-probed with the next antibody.

Incubation of SK-N-SH cells with 25 µM syringolin A resulted in a time-dependent accumulation of ubiquitinated proteins (FIG. 7G). The syringolin A treatment of SK-N-SH cells was further accompanied by a time-dependent increase in the protein levels of the tumor suppressor protein p53, a known target of the proteasome and important regulator of apoptosis and cell cycle progression (FIG. 7G), as shown previously in Example 4. The experiment was repeated three times with similar results.

Example 9

Glidobactin Inhibits the Eukaryotic Proteasome In Vitro

Figure 11:
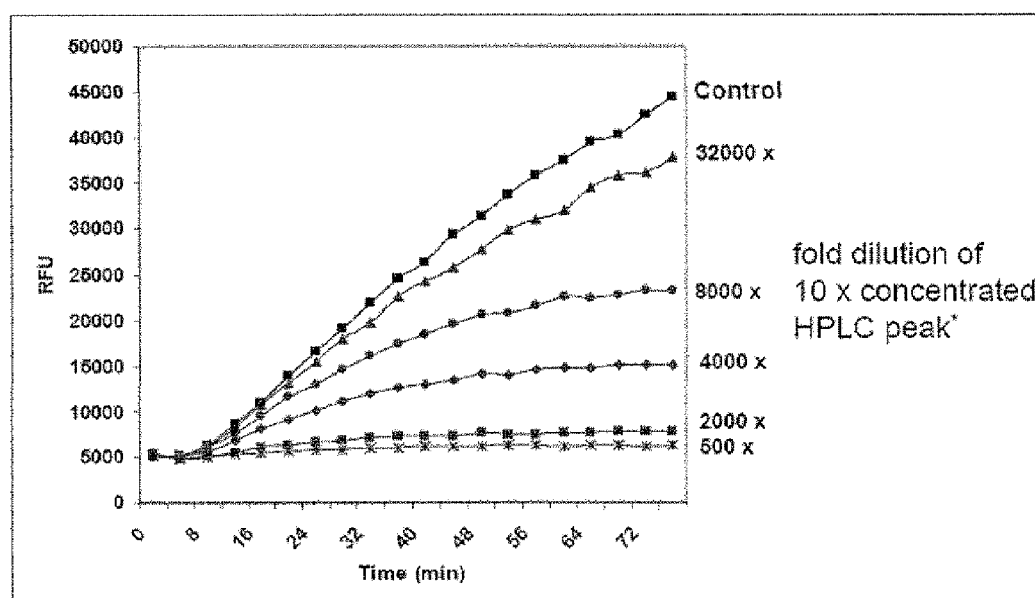
FIG. 11 is a line graph that depicts the inhibition of proteasome activity in vitro in the presence of increasing concentrations of glidobactin A.

Glidobactin was tested as a proteasome inhibitor using the 20S Proteasome Assay Kit for Drug Discovery AK-740 as described in Example 7. The fluorogenic substrates Suc-LLVY-AMC, Boc-LRR-AMC, and Z-LLE-AMC (BIO-MOL® International) were used to monitor chymotrypsin-like, trypsin-like, and caspase-like activities, respectively. A 100 µl reaction volume contained 2 µg/ml 20S proteasome, 100 µM substrate, and glidobactin isolated as described in Example 2 at final dilution values (of the 10× concentrated HPLC peak) of 500, 2000, 4000, 8000, and 32000×. The release of free AMC (7-amino-4-methylcoumarin) at 37° C. was monitored with an MWGt Sirius HT fluorescence microplate reader (BIO-TEK® Instruments) equipped with a 360 nm excitation and a 460 nm emission filter. As shown in FIG. 11, inhibition of the chymotrypsin-like activity of the proteasome increased with increasing concentrations (weaker dilutions) of the HPLC peak of glidobactin. A 500-fold dilution of glidobactin reduced proteasome activity to background levels. $K_i$ and $k_{association}$ values for GlbA were derived using the methods of Example 7 and an extinction coefficient of 35,000 $M^{-1}cm^{-1}$ at 261 nm in methanol to determine GlbA concentration. GlbA blocked the chymotrypsin-like activity irreversibly at low concentrations, whereas the trypsin-like activity was less sensitive (FIG. 7D) and the caspase-like activity was not inhibited at the concentrations tested (up to 20 µM).

Example 10

Elucidation of the Binding Mode of Syringolin A and Glidobactin to the Proteasome Using X-Ray Crystallography To elucidate the binding mode of syringolin. A and glidobactin A to the proteasome, each was cocrystallized with the yeast 20S proteasome. Crystals of the 20S proteasome were grown in hanging drops at 24° C. as described (Grail et al. 1997. *Nature* 386:463-471; Groll and Huber. 2005. *Methods Enzymol.* 398:329-336, each which is incorporated herein by reference in its entirety) and incubated for 60 min with syringolin A or glidobactin A. The protein concentration used for crystallization was 40 mg/ml in Tris-HCl (10 mM, pH 7.5) and EDTA (1 mM). The drops contained 3 µL of protein and 2 µL of the reservoir solution (30 mM magnesium acetate, 100 mM morpholino-ethane-sulphonic acid (pH 7.2) and 10% MPD), X-ray diffraction data to 2.9 Å for the yeast 20S proteasome:syringolin A and to 2.7 Å for the 20S proteasome: glidobactin A-complex were collected using synchrotron radiation with λ=1.05 Å on the BW6-beamline at DESY/Hamburg/Germany and with λ=1.0 Å on the BW6-beamline at SLS/Villingen/Switzerland, respectively. Crystals were soaked in cryoprotecting buffer (30% MPD, 20 mM magnesium acetate, 100 mM morpholino-ethane-sulfonic acid pH 6.9) and frozen in a stream of liquid nitrogen gas at 90 K (Oxford Cryo Systems). X-ray intensities were evaluated by using the DENZO program package (Otwinowski and Minor. 1997. *Methods Enzymol* 276:307-326) and data reduction was performed with CCP4 (Potterton et al. 2003. *Acta Crystallogr. D Biol. Crystallogr.* 59:1131-1137). The space group belongs to $P2_1$ with cell dimensions of about a=134 Å, b=302 Å, c=144 Å and β=112° (Table 1). The anisotropy of diffraction was corrected by an overall anisotropic temperature factor by comparing observed and calculated structure amplitudes using the program CNS (Brünger et al. 1998. *Acta Crystallogr. D Biol. Crystallogr.* 54: 905-921, which is incorporated herein by reference in its entirety). Electron density was improved by averaging and back transforming the reflections 10 times over the twofold non-crystallographic symmetry axis using the program package MAIN (Turk, D. 1992. "Improvement of a program for molecular graphics and manipulation of electron densities and its application for protein structure determination." Thesis, Technische Universitaet Muenchen, Muenchen, which is incorporated herein by reference in its entirety). Conventional crystallographic rigid body, positional and temperature factor refinements were carried out with CNS (Brünger et al., ibid) using the yeast 20S proteasome structure as starting model (Groll et al. 1997. *Nature* 386:463-471, which is incorporated herein by reference in its entirety) (Rcrys/Rfree=21.8/24.8). Model building was performed using the program MAIN.

Figure 12:
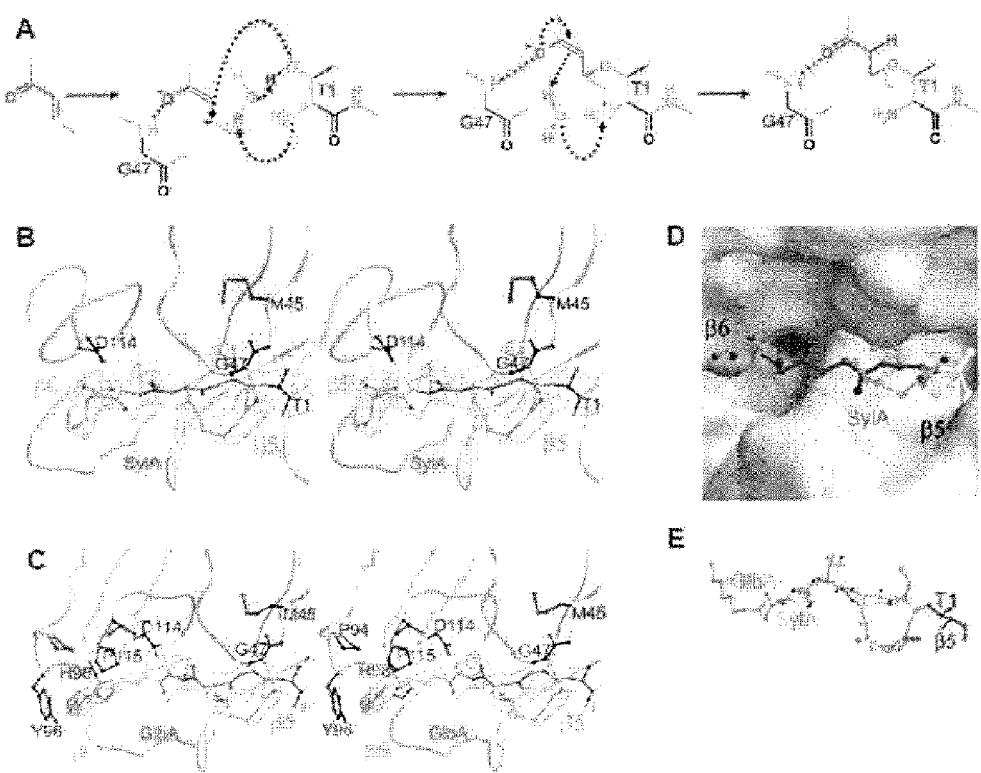
FIG. 12 includes illustrations that depict the mechanism of covalent binding of syringolin A and glidobactin A to the catalytic threonine of the proteasome active site (A), stereo representations of the chymotrypsin-like active site of the proteasome with bound syringolin A (B) or glidobactin (C), a surface model of syringolin A in the chymotrypsin-like active site, and a structural superposition of syringolin A with glidobactin A bound at this site.

Electron density maps calculated with phases after twofold averaging allowed a detailed interpretation of syringolin A (FIG. 12B), revealing that syringolin A covalently binds to the hydroxy group of the active site N-terminal threonine following a novel mechanism: Thr1Oγ of the proteasome performs a Michael-type 1,4-addition to the double bond located at C4 in the 12-membered ring system of the inhibitor. The resulting covalent ether bond with the 12-membered ring system causes the irreversible inhibition. This reaction is facilitated by Gly47N, which stabilizes the carbonyl anion of syringolin A in its activated transition intermediate state by hydrogen bonds (oxyanion hole) (FIG. 12A). Furthermore, the 12-membered ring structure of syringolin A containing the functional reactive group has a constrained conformation favoring high affinity binding for entropic reasons compared to flexible ligands (FIG. 12E). A stereo representation of the chymotryptic-like active site of the yeast 20S proteasome in complex with syringolin A is shown in FIG. 12. The functional reactive double bond at the 12-membered ring of syringolin A is combined with a dipeptide located in its close proximity (FIG. 1A). This dipeptide is essential for stabilization of syringolin A by formation of an antiparallel β-sheet at the substrate binding channel, which increases the mean residence time of the inhibitors at the active site for completing the covalent ether bond formation with Thr1Oγ.

The peptide structure of syringolin A is closely related to glidobactin A (GlbA; FIG. 1B), an acylated peptide derivative reported to have anti-fungal and anti-tumor activity (Oka et al. 1988. *J. Antibiot.* 41:1338-1350, which is incorporated herein by reference in its entirety). GlbA isolated from strain K481-B101 (ATCC 53080; DSM 7029) (Schellenberg et al. 2007. *Env Microbial.* 9:1640-1650, which is incorporated herein by reference in its entirety) was observed to inhibit proteasome activity as described in Example 9. The crystal structure of GlbA in complex with the proteasome was elucidated at 3.7 Å resolution yielding Rcrys/Rfree=23.4/262 (Table 1) (FIG. 12C). As expected, the complex structure revealed the same mechanism of inactivation of the chymotrypsin-like (FIG. 12D) and trypsin-like activities as SylA whereas GlbA did not bind to the caspase-like active site.

TABLE 1

X-ray diffraction data collection and refinement statistics

|  | 20S Proteasome:Syl A | 20S Proteasome:Glb A |
|---|---|---|
| Crystal parameters |  |  |
| Space group | P2₁ | P2₁ |
| Cell constants (one molecule/AU)[a] | a = 135.1 Å:1) = 302.0 Å, o = 143.8 Å; 13 = 112.9° | a = 133.2 Å; b = 301.8 Å, c = 143.1 Å; β = 111.9° |
| Data collection |  |  |
| Beamline | BW6, DESY | X06SA |
| Wavelength (Å) | 1.05 | 1.00 |
| Resolution range (Å)[b] | 99-2.9 (2.94-2.89) | 50-2.7 (2.87-2.7) |
| No. observations | 807967 | 945712 |
| No. unique reflections[c] | 252555 | 368665 |
| Completeness (%)[b] | 98.6 (99.7) | 96.0 (85.8) |
| $R_{merge}$ (%)[b,d] | 13.5 (52.5) | 12.5 (37.3) |
| I/σ (I)[b] | 9.1 (2.2) | 13.3 (3.0) |
| Refinement (CNS) |  |  |
| Resolution range (Å) | 15-2.90 | 15-2.7 |
| No. refl. working set | 238982 | 263455 |
| No. refl. test set | 12541 | 13733 |
| No. non hydrogen | 49548 | 49548 |
| Solvent water | 1018 | 1336 |
| Inhibitor (non hydrogen) | 210 | 148 |
| $R_{work}/R_{free}$ (%)[f] | 21.8/24.8 | 23.4/26.2 |
| rmsd bond (Å)/(°)[g] | 0.007/1.33 | 0.007/1.35 |
| Average B-factor (Å²) | 68.2 | 50.1 |
| Ramachandran Plot (%)[h] | 94.0/5.2/0.9 | 93.8/5.4/0.8 |

[a]Asymmetric unit.
[b]The values in parentheses of resolution range, completeness, $R_{merge}$ and I/σ (I) correspond to the last resolution shell.
[c]Friedel pairs were treated as different reflections.
[d]$R_{merge}(I) = \Sigma_{hkl}\Sigma_j |I(hkl) - I(hkl)|/[\Sigma_{hkl} I_{hkl}]$, where $I(hkl)_j$ is the jth measurement of the intensity of reflection hkl and <I(hkl)> is the average intensity.
[e]Figure of merit = $\Sigma_\alpha P(\alpha)^{i\alpha}/\Sigma\alpha P(\alpha)$, after density modification where α is the phase and P(α) is the phase probability distribution.
[f]$R = \Sigma_{hkl}||F_{obs}| - |F_{calc}||/\Sigma_{hkl}|F_{obs}|$, where Rfree is calculated without a sigma cutoff for a randomly chosen 5% of reflections, which were not used for structure refinement, and Rwork is calculated for the remaining reflections.
[g]Deviations from ideal bond lengths/angles.
[h]Number of residues in favored region/allowed region/outlier region.

Example 11

Glidobactin Inhibits Proteasome Activity in Neuroblastoma and Ovarian Cancer Cells In this study, glidobactin A (GlbA) as well as syringolin A (SylA) were assayed for its ability to inhibit the in vivo proteasome activity in SK-N-SH neuroblastoma cells and SKOV3 human ovarian cancer cells.

The cell culture-based proteasome inhibition assay was performed as previously described (Groll et al. 2008. *Nature* 452:755-758, which is incorporated herein by reference in its entirety). Briefly, wells of white-walled 96-well microtiter cell culture plates were seeded at a density of 1×10⁴ cells/well (SK-N-SH) or 5×10³ cells/well (SKOV3) in 90 μl. After 24 hours, 10 μl GlbA or SylA were added at increasing concentrations (0-100 μM) and incubated for 2 hours. The proteasome inhibitor epoxomicin (0-1 μM) and the apoptosis inducing agent cerulenin (0-50 μg/ml) (Geerts, et al. 2007. *Clin Cancer Res* 13(21):6312-6319); Heiligtag, et al. 2002. *Cell Death Differ* 9:1017-1025; Meng, et al. 1999. *PNAS* 96:10403-10408, each of which is incorporated herein by reference in its entirety) were used as positive and negative controls, respectively. Microtiter plates were then equilibrated to room temperature for 15 min before adding 100 μl of proteasome Glo™ reagent (containing bioluminescent substrate Suc-LLVY-aminoluciferin) per well. Luminescence was measured on a Dynex MLX luminometer, according to the manufacturer's instructions (Promega).

Figure 13:
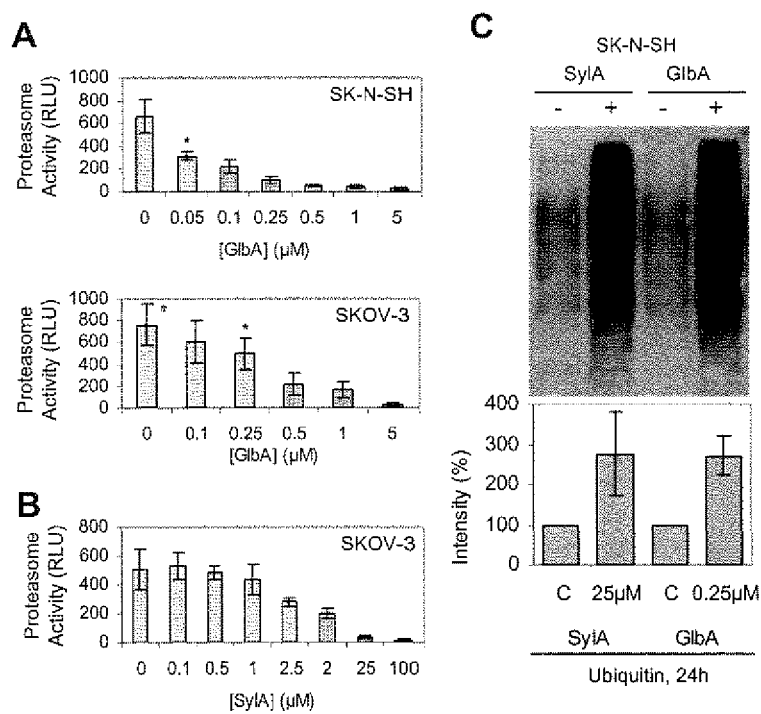
FIG. 13 includes bar graphs and a Western blot that illustrate the ability of the glidobactin A and syringolin A to inhibit proteasome activity and increase levels of ubiquitinated protein in SH-N-SH neuroblastoma cells and SKOV3 ovarian cancer cells.

As shown in FIG. 13A, GlbA significantly inhibited the proteasomal activity in SK-N-SH and SKOV3 cells in a dose-dependent manner, with an $IC_{50}$ of 0.055 μM and 0.25 μM, respectively. SylA inhibited the proteasomal activity in SKOV3 cells in a dose-dependent manner (FIG. 13B), in a fashion similar to what was previously observed with SK-N-SH cells (Groll et al. 2008. supra). The $IC_{50}$ value for SKOV3 cells was at 4.03 μM and comparable with the value previously determined for SK-N-SH cells at 1.43 μM. Epoxomicin, an established proteasome inhibitor and cerulenin, an apoptosis-inducing agent, were included as a positive and negative controls, respectively (not shown). Together, these results indicate that both GlbA and SylA inhibit the proteasomal activity in SK-N-SH and SKOV3 cells. Remarkably, GlbA was approximately 26-fold (SK-N-SH) and approximately 16-fold (SKOV3) more potent than SylA in this assay.

To further examine the inhibitory effect, whole cell lysates of GlbA-treated or untreated control cells were analyzed by Western blot and ubiquitinated proteins detected at endogenous levels. GlbA-treated cells showed a marked increase of ubiquitinated proteins compared to untreated control cells (FIG. 13C), SylA was included for comparison and to confirm previous observations (Groll et al. 2008. supra). The quantification revealed a 3-fold increase of ubiquitinated proteins in SK-N-SH cells after 24 hours of treatment with GlbA or SylA. Of note, GlbA induced comparable effects at a 100-fold lower concentration. Together, these results demonstrate that GlbA and SylA induce comparable effects, and GlbA appears to be significantly more potent in two independent cell-based assays.

Example 12

Glidobactin Induces Anti-Proliferative Effects and Morphological Changes in Neuroblastoma and Ovarian Cancer Cells Syringolin A (SylA) was shown to inhibit the proliferation of mammalian cells including SK-N-SH and SKOV3 cells (Example 3), and the $EC_{50}$ was determined to be ~20 μM (Coleman et al. 2006. supra). To determine the effect of glidobactin A (GlbA) on cell proliferation, SK-N-SH and SKOV3 cells were treated at different concentrations of GlbA for 48 hours.

The CellTiter 96 Aqueous One solution Cell Proliferation Assay (2-(4,5-dimethylthiazol-2-yl)-5-(3-carboxymethoxyphenyl)-2-(4-sulfophenyl)-2H-tetrazolium, inner salt; MTS) (Promega, San Luis Obispo, Calif.) was used to determine the viability of cells treated with GlbA and SylA. Briefly, SK-N-SH and SKOV3 cells were seeded in clear, 96 well plates, as described (Example 11), and cultured for 18-24 hours. Ten μl GlbA or SylA were added at different concentrations (0-100 μM) and incubated for 48 hours. After the experiment, 20 uL of tetrazolium CellTiter 96 Aqueous One Solution Reagent was added to wells, incubated for 75-150 min. at 37° C. The absorbance was measured at 490 nm using a Perkin Elmer HTS7000 Plus bioassay reader.

Figure 14:
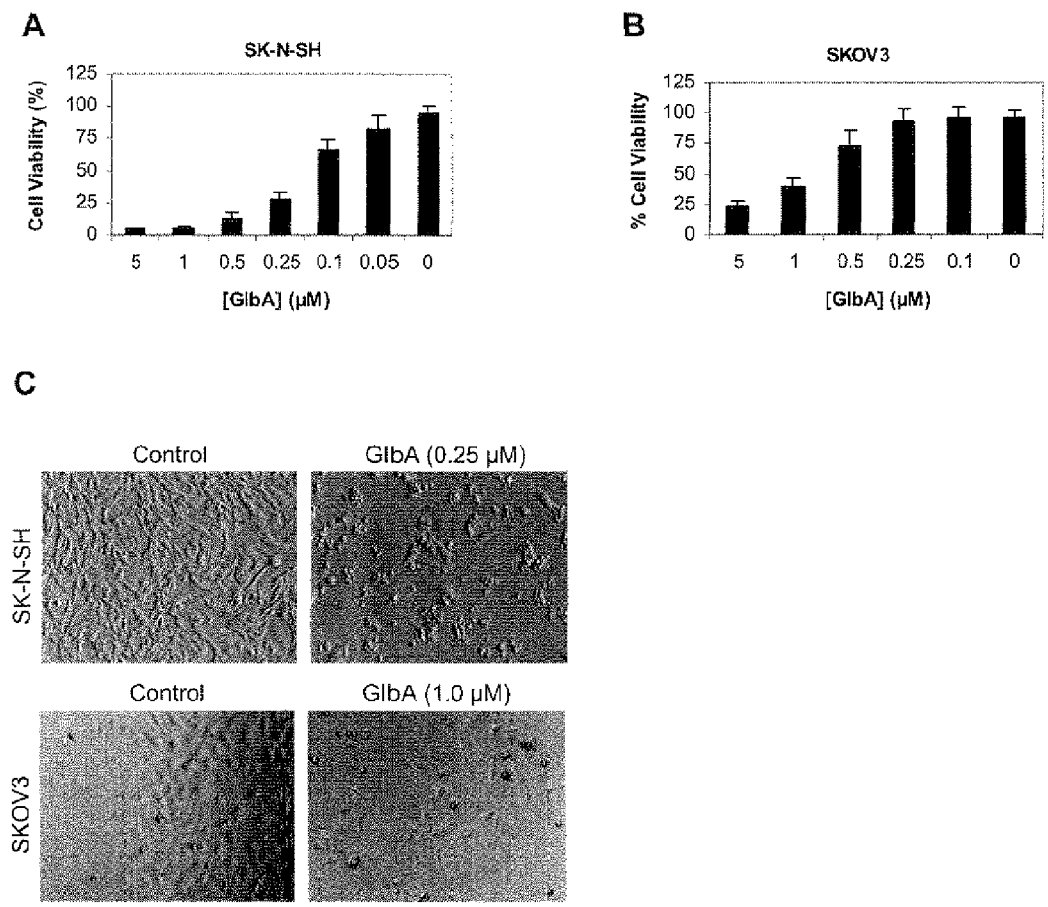
FIG. 14 includes bar graphs and microscope images that illustrate the effect of glidobactin A and syringolin A on cell viability and the effect of glidobactin A on cell morphology in SH-N-SH neuroblastoma cells and SKOV3 ovarian cancer cells.
Figure 15:
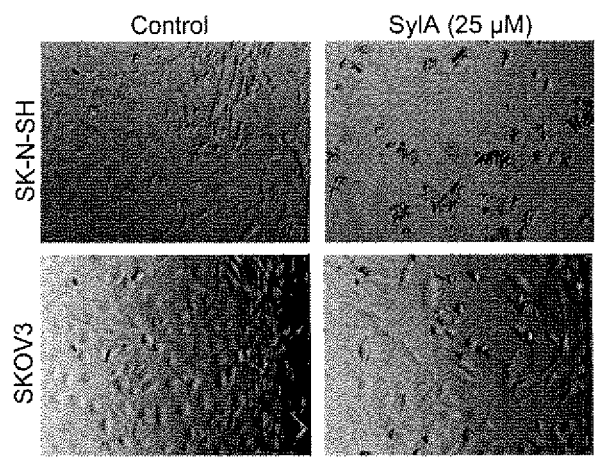
FIG. 15 includes microscope images that show the effect of syringolin A on cell morphology in SH-N-SH neuroblastoma cells and SKOV3 ovarian cancer cells.

GlbA reduced the proliferation rate of both SK-N-SH and SKOV3 cells in a dose-dependent manner with an $EC_{50}$ of ~0.14 μM and ~0.80 μM, respectively (FIGS. 14A and 14B). The $EC_{50}$ values of GlbA were compared with values from previous studies with SylA and showed that GlbA was about 143-fold (SK-N-SH) and 25-fold (SKOV3) more effective than SylA (Table 2). At the microscopic level, treatment with GlbA induced severe morphological changes in both SK-N-SH and SKOV3 cells (FIG. 14C). The typically triangular-shaped SK-N-SH cells appeared rounded and detached from the culture plates after 48 hours. Treated SKOV3 cells also began to lose their typical flat appearance and were less dense, although fewer floating cells were observed after 48-hour treatment. Similar effects were induced by SylA but required significantly higher drug concentrations (FIG. 15).

The results indicate that GlbA can inhibit proliferation and induce morphological changes in cancer cell lines.

TABLE 2

| | $EC_{50}$ values $EC_{50}$ (μM) | |
|---|---|---|
| | SK-N-SH | SKOV3 |
| GlbA | ~0.14 | ~0.8 |
| SylA | ~20 | ~20 |

Example 13

Determination of Potential Cytotoxic Effects

Determination of potential cytotoxic effects by GlbA and/or {{??}} was carried out by using the Cytox-Glo cytotoxicity assay, which measures "dead cell proteases" from cells that have lost membrane integrity. Briefly, cells were treated with a single concentration of compound for 48 hours in a final volume of 100 μl, after which 50 μl of AAF-Glo luminogenic peptide substrate (alanyl-alanyl-phenylalanyl-aminoluciferin) was added to each well and incubated for 15 min at room temperature. The luminescence was measured by a Dynex MLX luminometer to give a reading of cells with damaged membranes. Next, 50 μl of digitonin was added to each well and the samples incubated for 15 minutes at room temperature. Luminescence was measured a second time to determine total cell number. Controls included cells with vehicle only, media, and media with compound.

Figure 16:
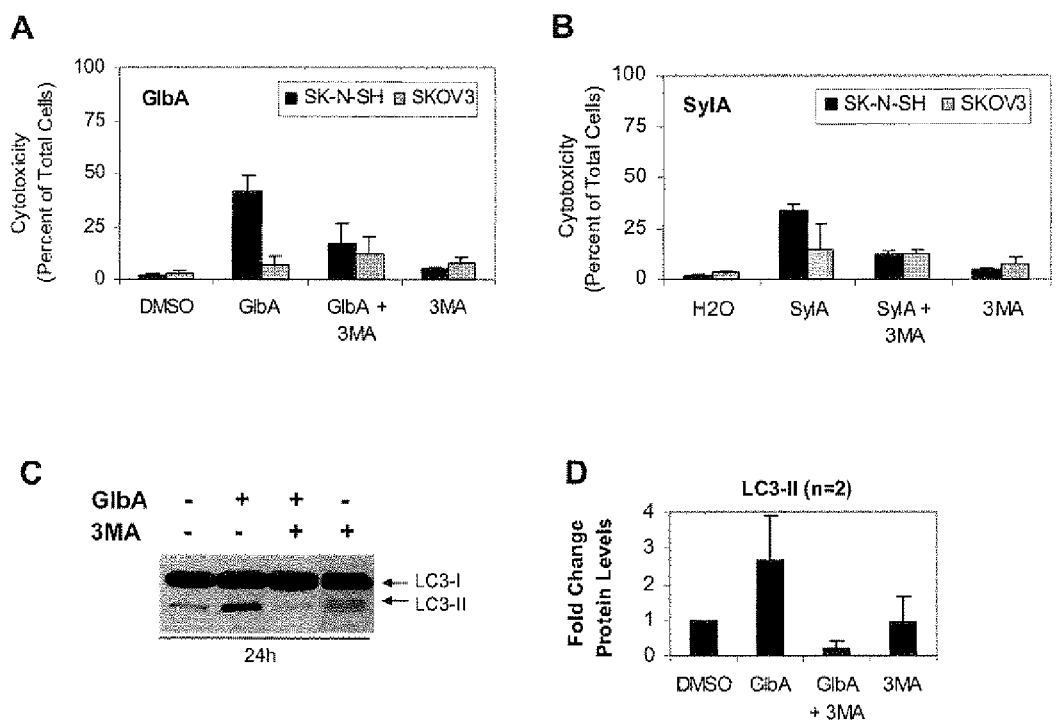
FIG. 16 includes bar graphs and a Western blot that show the cytotoxic effects of glidobactin A and syringolin A in the presence or absence of an autophagy inhibitor on SH-N-SH neuroblastoma cells and SKOV3 ovarian cancer cells.

SK-N-SH cells were treated with 0.25 μM GlbA or 25 μM SylA and SKOV3 cells were treated with 1.0 μM GlbA or 25 μM SylA. As illustrated in FIGS. 16A and 16B, control cells (treated with DMSO and $H_2O$ representing GlbA and SylA controls, respectively) were viable and no cytotoxicity was detected. In SK-N-SH cell, GlbA or SylA exhibited about 40% and 30% cytotoxicity, respectively. In contrast, GlbA- or SylA-treated SKOV3 cells were less affected with relatively low levels of cytotoxicity.

Example 14

Glidobactin A and Syringolin A Induce Autophagy in Neuroblastoma Cells

To determine if autophagy plays a role in GlbA/SylA-induced cell death, levels of cytotoxicity in cells pre-treated with 3-methyladenine (3-MA), an established autophagy inhibitor, were measured using the assay described in Example 12.

Unexpectedly, both GlbA- and SylA-induced cytotoxicity in SK-N-SH cells was significantly reduced in the presence of 3-MA (FIGS. 16A and 16B). Interestingly, it was also observed by light microscope that 3-MA control cells showed very few rounded cells, and the density was sparse compared to the untreated control cells, indicating that 3-MA suppresses SK-N-SH cell proliferation without killing cells after 48 hours. Moreover, cells that were pre-treated with 3-MA for 3 hours prior to GlbA or SylA treatment appeared to have similar cell density as the 3-MA control cells, and fewer rounded cells than the treated cells after 48 hours (not shown).

To verify whether autophagy is induced in GlbA-treated cells, levels of microtubule-associated protein 1 light chain 3 (LC3), a reliable marker of autophagosomes, were measured. Immunoblotting of LC3 typically reveals two bands, LC3-I (18 kDa) and LC3-II (16 kDa), and the amount of LC3-II correlates with the number of autophagosomes present in cells. Therefore, this characteristic conversion of LC3 can be used to monitor autophagic activity. SK-N-SH cells were treated with GlbA in the presence or absence of 3-MA, and cell lysates were probed with LC3. It was found that GlbA-treated cell lysates contained larger amounts of LC3-II as compared to untreated control cells (FIGS. 16C and 16D). Pre-treatment of cells with autophagy inhibitor 3-MA reverted GlbA-induced autophagy and confirmed the specificity of reaction. Treatment with 3-MA alone did not alter the conversion of LC3. Similar but less pronounced effects were observed with SylA (not shown).

In summary, these results demonstrate that GlbA and SylA strongly inhibit cell proliferation and induce some cytotoxicity in SK-N-SH cells, but not SKOV3 cells. Remarkably, 3-MA suppressed GlbA and SylA-induced cytotoxicity in SK-N-SH cells, and the conversion of LC3 confirmed the onset of autophagy in both GlbA- and SylA-treated cells.

Example 15

Glidobactin A Induces Apoptosis in Neuroblastoma and Ovarian Cancer Cells

The role of glidobactin A (GlbA) in apoptosis and its correlation with autophagy has not previously been examined.

Therefore, in a series of experiments, cell lysates of SK-N-SH cells were treated with GlbA in the presence and absence of the autophagy inhibitor 3-methyladenine (3-MA) and probed for poly ADP-ribose polymerase (PARP). The cleavage of PARP produces a smaller 89 kDa fragment which is indicative of late apoptosis.

Figure 17:
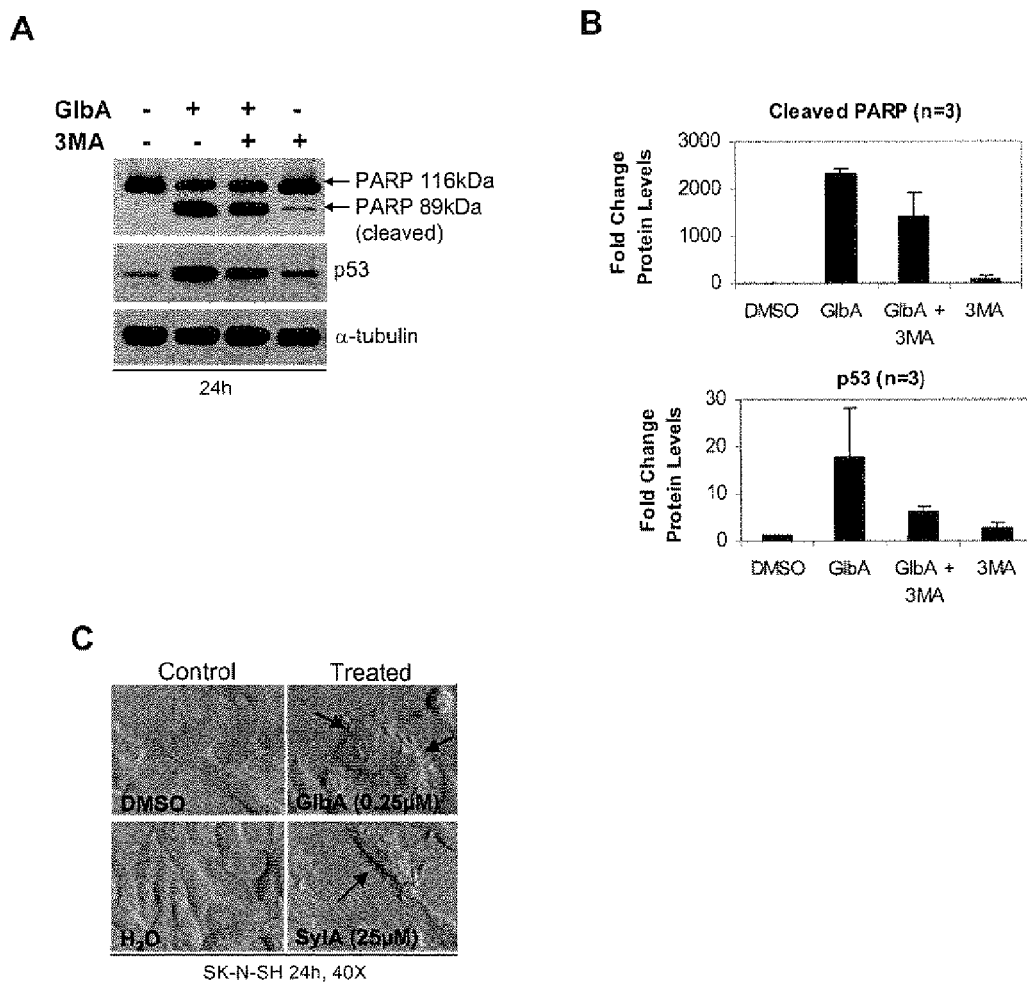
FIG. 17 includes Western blots, bar graphs and microscope images that illustrate the effect of glidobactin A treatment on. PARP cleavage and total p53 protein levels in SH-N-SH neuroblastoma cells in the presence or absence of an autophagy inhibitor.

PARP cleavage was observed in GlbA-treated SK-N-SH cells, and 3-MA treatment slightly reduced this effect (FIG. 17A). 3-MA alone had no effect on PARP cleavage and was comparable to untreated control cells. The total protein levels of tumor suppressor protein p53, a key protein of apoptosis, were also measured. A strong accumulation of p53 was observed, and 3-MA partially reduced the GlbA-induced p53 levels (FIG. 17A). The protein levels of cleaved PARP and p53 were quantified as depicted in FIG. 17B. GlbA-treated cells were also examined by microscopy and revealed the presence of membrane blebbing, a typical sign of apoptosis. For comparison, cells were treated with SylA and revealed similar apoptotic effects (FIG. 17C).

Figure 18:
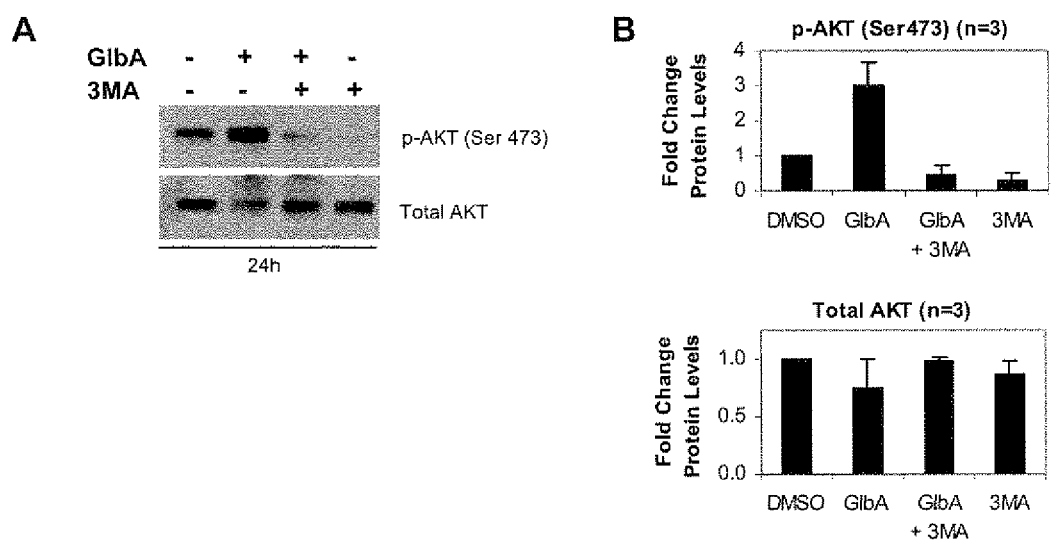
FIG. 18 includes Western blots and bar graphs that illustrate the effect of glidobactin A in the presence or absence of an autophagy inhibitor on total Akt/PKB levels and its phosphorylation status at reside Ser473 in SH-N-SH neuroblastoma cells.
Figure 19:
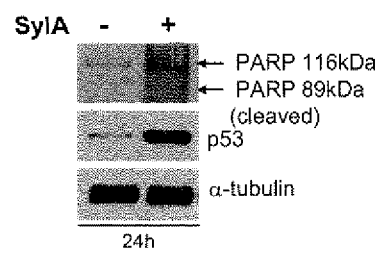
FIG. 19 is a Western blot that illustrates the effect of syringolin A treatment on PARP cleavage and total p53 protein levels in SH-N-SH neuroblastoma cells.
Figure 20:
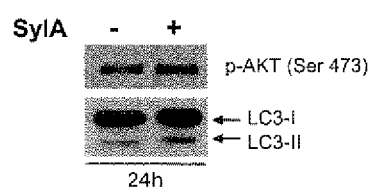
FIG. 20 is a Western blot that illustrates the effect of syringolin A on total Akt/PKB levels, its phosphorylation status at reside Ser473, and microtubule-associated protein 1 light chain 3 (LC3) levels in SH-N-SH neuroblastoma cells.

Since Akt/PKB is a well-characterized anti-apoptotic protein, total Akt/PKB levels were measured in treated cells in addition to determining the protein's phosphorylation status at residue Ser473, which is indicative of its activity. SK-N-SH cells were treated with GlbA in the presence or absence of 3-MA, and cell lysates were analyzed for Akt/PKB. Interestingly, Akt/PKB was phosphorylated at Ser473 after GlbA treatment, and the phosphorylation was prevented by pretreatment of cells with 3-MA (FIGS. 18A and 18B). Total Akt/PKB levels did not significantly change, although a slight decrease in GlbA-treated cells was observed.

Example 16

Initial Dose and Toxicity Studies of Syringolin and Glidobactin Compounds in a Mouse Model of Human Neuroblastoma Maximum tolerated dose and toxic effects of SylA, GlbA and/or derivatives thereof are investigated in a mouse model of human neuroblastoma.

The TH-MYCN transgenic mouse is a well-established neuroblastoma mouse model (Hansfored, et al. 2004. *PNAS* 101(34):12664-12669; Weiss, et al. 2007. *Cancer Res* 67(19): 9435-9442; Weiss, et al. 2000. *Cancer Res* 6"2483-2487, each of which is incorporated herein by reference in its entirety). The tumors are caused by targeted expression of MYCN to the neural crest under the control of the rat tyrosine hydroxylase promoter, where the mice develop a tumor phenotype that closely resembles the human disease. The tumors in this strain of mouse generally develop in the abdominal and thoracic areas. TH-MYCN breeder pairs are supplied as hemizygote (129×1/SvJ-Tg(TH-MYCN)41Waw) and a wild type mate (129×1/SvJ).

Test compounds are administered to wild type and hemizygous or heterozygous mice at different doses (plus vehicle to an untreated control group). Four (4) mice per dose are tested. The test compounds are injected by tail vein (i.v.) or intraperitoneally (i.p.) every 3 to 7 days, depending on availability of compound. In the event of i.p. injection, use of micropumps is optionally considered. Micropumps can be implanted according to the manufacturer's protocol in and set to administer test compounds as separate doses. For example, micropumps can be set to provide an hourly release of compound or as a continual dose for between 3-6 weeks. To determine metabolism and absorption of test compounds, approximately 30-50 μL of blood is collected within 15 minutes after the first i.v. or i.p. injection, with additional volumes of 30-50 μL collected three days after compound administration. However, no more than 10% of blood volume is removed from the mice every two weeks.

An exemplary administration protocol of test compounds is as follows in Table 3:

TABLE 3

Exemplary Dosages
Administered every 3 to 7 days by i.v. or i.p*. means for between 3 to 6 weeks

|  | Vehicle | Volume | Dose 1 [mg/kg] | Dose 2 [mg/kg] | Dose 3 [mg/kg] | Dose 4 [mg/kg] | Dose 5 [mg/kg] |
|---|---|---|---|---|---|---|---|
| SylA | 0.9% Saline | i.v. = 0.1 mL i.p. = 0.5 mL | 4 | 8 | 12 | 16 | 20 |
| SylA Derivative | 0.9% Saline containing 10% DMSO | i.v. = 0.1 mL i.p. = 0.5 mL | 4 | 8 | 12 | 16 | 20 |
| GlbA | 0.9% Saline containing 10% DMSO | i.v. = 0.1 mL i.p. = 0.5 mL | 0.1 | 0.5 | 1.5 | 3 | 8 |
| GlbA Derivative | 0.9% Saline containing 10% DMSO | i.v. = 0.1 mL i.p. = 0.5 mL | 0.1 | 0.5 | 1.5 | 3 | 8 |
| Restraint i.p. |  | Handheld |  |  |  |  |  |
| Restraint i.v. |  | Plastic mouse restraint box |  |  |  |  |  |

*Micropumps can be used for i.p. administration of compound

Example 17

Syringolin and Glidobactin Compounds Reduce Tumor Size in a Mouse Model of Human Neuroblastoma The tumor reduction capacity of SylA, GlbA and/or derivatives thereof are investigated in a mouse model of human neuroblastoma.

Test compounds are administered to homozygous mice at a dose that is developed based upon the results of the initial dose and toxicity study (Example 15). Two to four doses per compound are administered by i.p. and/or i.v. methods into homozygous mice when palpable tumors begin to form. Vehicle is delivered is delivered as a control. Further doses are administered thereafter every 72 hours for 3 to 6 weeks.

Between eight to twelve mice are tested in the study for administration of each compound. During administration of the test compounds, the mice are visually and manually inspected for assessment of tumor size as well as the development or mitigation of tumor-related symptoms. At the conclusion of the study, the mice are sacrificed and tumor size and number of tumors are assessed. It is observed that administration of SylA and GlbA compounds and derivatives thereof are effective in reducing both the size and number of tumors in treated mice compared to untreated mice. The results indicate that SylA, GlbA and derivatives thereof are effective in reducing tumor size.

Example 18

Chemoprevention in a Mouse Model of Human Neuroblastoma

The tumor reduction capacity of SylA, GlbA and/or derivatives thereof are investigated in a mouse model of human neuroblastoma for the ability to prevent tumor formation.

Treatment regimen is similar to that described in Example 16. Test compounds are administered to homozygous mice at a dose that is developed based upon the results of the initial dose and toxicity study (Example 15). Two to four doses per compound are administered by i.p. and/or i.v. methods into homozygous mice at week 4 or 5 (in advance of tumor development, which occurs closer to week 7). Vehicle is delivered as a control. Further doses are administered every 72 hours thereafter for 3 to 6 weeks. Between eight to twelve mice are tested in the study for administration of each compound. During administration of the test compounds, the mice are visually and manually inspected for assessment of tumor size as well as the development or mitigation of tumor-related symptoms. At the conclusion of the study, the mice are sacrificed and tumor size and number of tumors are assessed. It is observed that homozygous mice treated with administration of SylA and GlbA compounds and derivatives thereof have fewer or no tumors compared to untreated mice. The results indicate that SylA, GlbA and derivatives thereof are effective in preventing the formation of tumors.

Example 19

Reduction of Tumor Size in Human Subjects Diagnosed with Blood Cancers

A human subject is diagnosed with a type of blood cancer. Initial measurement of tumor size and/or volume as well as determination of the number of tumors in the patient are obtained. The patient is treated with a composition comprising the compounds disclosed herein at a dose of from 1.2 mg/m$^2$ to 1.8 mg/m$^2$, depending on the patient's tolerance for the composition. The composition is administered as a cycle of two to three times weekly for two weeks, followed by a one-week break. Additional cycles of composition administration are provided as needed based on ongoing clinical monitoring of the patient. It is observed that administration of the compositions disclosed herein is effective in reducing the size and number of tumors in the patient.

Example 20

Reduction of Tumor Size in Human Subjects Diagnosed with Ovarian Cancer

A human subject is diagnosed with ovarian cancer. Initial measurement of tumor size and/or volume as well as determination of the number of tumors in the patient are obtained. The patient is treated with a composition comprising a syrbactin compound at a dose of from 1.2 mg/m$^2$ to 1.8 mg/m$^2$, depending on the patient's tolerance for the composition. The composition is administered as a cycle of two to three times weekly for two weeks, followed by a one-week break. Additional cycles of composition administration are provided as needed based on ongoing clinical monitoring of the patient. It is observed that administration of the composition is effective in reducing the size and number of tumors in the patient.

Example 21

Reduction of Tumor Size in Human Subjects Diagnosed with Neuroblastoma

A human subject is diagnosed with neuroblastoma. Initial measurement of tumor size and/or volume as well as determination of the number of tumors in the patient are obtained. The patient is treated with a composition comprising a syrbactin compound at a dose of from 1.2 mg/m$^2$ to 1.8 mg/m$^2$, depending on the patient's tolerance for the composition. The composition is administered as a cycle of two to three times weekly for two weeks, followed by a one-week break. Additional cycles of composition administration are provided as needed based on ongoing clinical monitoring of the patient. It is observed that administration of the composition is effective in reducing the size and number of tumors in the patient.

Example 22

Synergy in Combination with Alpha-Difluoromethylornithine for Reducing Tumor Size Subjects having neoplastic tumors are provided. For each subject, initial measurement of tumor size and/or volume as well as determination of the number of tumors are obtained. One group of subjects is treated with a composition comprising a syrbactin compound, at a dose of from 1.2 mg/m$^2$ to 1.8 mg/m$^2$, and alpha-difluoromethylornithine (DFMO). A second group of subjects is treated with a composition comprising the syrbactin compound, at the same dose, without DFMO. A third group of subjects is treated with a composition containing DFMO but no syrbactin compound. A fourth group of subjects is treated with a composition that does not include either the syrbactin compound or DFMO. The composition is administered as a cycle of two to three times weekly for two weeks, followed by a one-week break. Additional cycles of composition administration are provided as needed based on ongoing clinical monitoring of the subjects. It is observed that administration of the composition comprising the syrbactin compound and DFMO provides a synergistic effect in reducing the size and number of tumors in the first group of subjects relative to the effect found in the second, third and fourth group of subjects.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the invention disclosed herein. Still further variations and alternate elements will be apparent to one of skill in the art. Among these variations, without limitation, are the specific number of antigens in a screening panel or targeted by a therapeutic product, the type of antigen, the type of cancer, and the particular antigen(s) specified. Various embodiments of the invention can specifically include or exclude any of these variations or elements.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. The skilled artisan can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the invention disclosed herein. Other modifications that can be employed can be within the scope of the invention. Thus, by way of example, but not of limitation, alternative configurations of embodiments of the invention can be utilized in accordance with the teachings herein. Accordingly, embodiments of the invention are not limited to that precisely as shown and described.

The invention claimed is:

1. A method for reducing tumor size or number by inhibiting proteasome activity in a population of cancerous cells comprising:
(i) contacting a population of cancerous cells with an amount of an analog of the following compound

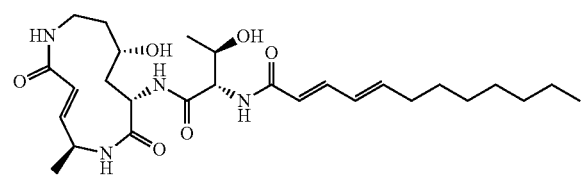 [SMILES: CCCCCCC/C=C/C=C/C(=O)N[C@H](C(=O)N[C@H]1C[C@@H](O)CCNC(=O)/C=C/[C@H](C)NC1=O)[C@@H](C)O]

comprising the 12-membered ring structure having a double bond at the 3,4 position, or
an amount of an analog of the following compound

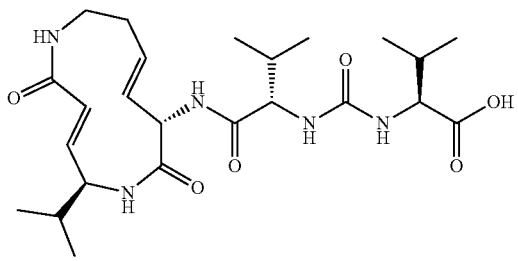 [SMILES: CC(C)[C@H](NC(=O)N[C@H](C(=O)N[C@H]1/C=C/CCNC(=O)/C=C/[C@H](C(C)C)NC1=O)C(C)C)C(=O)O]

comprising the 12-membered ring structure having a double bond at the 3,4 position,
said contacting being effective to inhibit the activity of a β5 catalytic subunit of the proteasome of said population of cancerous cells, wherein the double bond at the 3,4 position of the 12-membered ring covalently attaches the compound to the threonine residue of the β5 subunit of the catalytic site of the proteasome of said cancerous cells;

(ii) confirming inhibition of proteasome activity;

(iii) assessing the tumor size; and (iv) repeating steps (i) to (iii) until a reduction in tumor size or number is observed.

2. The method of claim 1, wherein confirming inhibition of proteasome activity comprises detecting inhibition at least one type of proteasomal activity selected from the group consisting of: activity at the β5 catalytic subunit of a proteasome, activity at the β2 catalytic subunit of a proteasome, and activity at the β1 catalytic subunit of a proteasome; detecting the accumulation of ubiquitinated proteins; and performing co-crystallization assays.

3. The method of claim 1, wherein the compound further inhibits activity at the β2 catalytic subunit of a proteasome of the cell.

4. The method of claim 1, wherein the compound further inhibits activity at the β1 catalytic subunit of a proteasome of the cell.

5. The method of claim 1, wherein confirming inhibition of proteasome activity comprises detecting inhibition of activity at the β5 catalytic subunit of a proteasome.

6. The method of claim 1, wherein confirming inhibition of proteasome activity comprises detecting inhibition of activity at the β2 catalytic subunit of a proteasome.

7. The method of claim 1, wherein confirming inhibition of proteasome activity comprises detecting inhibition of activity at the β1 catalytic subunit of a proteasome.

\* \* \* \* \*